(12) United States Patent
Kim et al.

(10) Patent No.: US 9,851,314 B2
(45) Date of Patent: Dec. 26, 2017

(54) CHIRAL METAL COMPLEX AND USE THEREOF FOR ANALYZING CHIRALITY OF CHARGED COMPOUND BY $^1$H NMR SPECTROSCOPY

(71) Applicants: KOREA ADVANCED INSTITUTE OF SCIENCE AND TECHNOLOGY, Daejeon (KR); INSTITUTE FOR BASIC SCIENCE, Daejeon (KR)

(72) Inventors: Hyunwoo Kim, Daejeon (KR); Min-Seob Seo, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 229 days.

(21) Appl. No.: 14/947,538

(22) Filed: Nov. 20, 2015

(65) Prior Publication Data
US 2017/0052131 A1  Feb. 23, 2017

(30) Foreign Application Priority Data

Aug. 19, 2015 (KR) .................. 10-2015-0116903

(51) Int. Cl.
| | | |
|---|---|---|
| C07C 51/41 | (2006.01) | |
| G01N 24/08 | (2006.01) | |
| C07C 215/50 | (2006.01) | |
| C07F 7/28 | (2006.01) | |
| C07F 5/00 | (2006.01) | |
| C07F 5/06 | (2006.01) | |

(52) U.S. Cl.
CPC .......... G01N 24/08 (2013.01); C07C 215/50 (2013.01); C07F 5/003 (2013.01); C07F 5/069 (2013.01); C07F 7/28 (2013.01); C07B 2200/07 (2013.01); C07C 2601/14 (2017.05)

(58) Field of Classification Search
CPC .......... C07C 215/50; C07F 5/069; C07F 7/28
USPC ........................................... 556/6
See application file for complete search history.

(56) References Cited

U.S. PATENT DOCUMENTS

2008/0234502 A1* 9/2008 Kondo .................. C07C 215/50
549/396

FOREIGN PATENT DOCUMENTS

| KR | 100170925 | 10/1998 |
|---|---|---|
| KR | 100233960 | 9/1999 |

OTHER PUBLICATIONS

Lei Gong et al., "Chiral-Auxiliary-Mediated Asymmetric Synthesis of Ruthenium Polypyridyl Complexes," Fujian Provincial Key Laboratory of Chemical Biology, Department of Chemical et al., Mar. 26, 2013, Published on the Web Jun. 3, 2013 www.pubs.acs.org/accounts.

Lei Gong et al., "Isomerization-Induced Asymmetric Coordination Chemistry: From Auxiliary Control to Asymmetric Catalysis," DOI: 10.1002/anie.201003139, Angew. Chem. Int. Ed. 2010, 49, 7955-7957, 2010 Wiley-VCH Verlag GmbH & Co. KGaA, Weinheim, http://dx.doi.org/10.1002/anie.201003139.

James A. Dale et al., "a-Methoxy-a-trifluoromethylphenylacetic Acid, a Versatile Reagent for the Determination of Enantiomeric Composition of Alcohols and Amines," Department of Chemistry, Stanford University, Stanford, California, Received Mar. 6, 1969, Val. 34, No. 9, Sep. 1969.

* cited by examiner

*Primary Examiner* — Rosalynd Keys
*Assistant Examiner* — Kofi Adzamli
(74) *Attorney, Agent, or Firm* — Hauptman Ham, LLP

(57) ABSTRACT

Provided are novel ligand, a chiral metal complex including the same, and a use of the chiral metal complex for analyzing the chirality of a charged compound by $^1$H NMR spectroscopy. The chiral metal complex of the present invention may be used as the chiral solvating agent to conveniently analyze the optical purity of charged compounds such as various amine derivatives, carboxylic acid derivatives, cyanohydrin derivatives and charged metal complexes by $^1$H NMR spectroscopy.

7 Claims, 6 Drawing Sheets

CHIRAL METAL COMPLEX AND USE THEREOF FOR ANALYZING CHIRALITY OF CHARGED COMPOUND BY $^1$H NMR SPECTROSCOPY

CROSS-REFERENCE TO RELATED APPLICATIONS

This application claims priority under 35 U.S.C. §119 to Korean Patent Application No. 2015-0116903, filed on Aug. 19, 2015, in the Korean Intellectual Property Office, the disclosure of which is incorporated herein by reference in its entirety.

TECHNICAL FIELD

The following disclosure relates to a novel ligand, a chiral metal complex including the same, and a use of the chiral metal complex for analyzing chirality of a charged compound by $^1$H NMR spectroscopy. The chiral metal complex of the present invention may be used as a chiral solvating agent to conveniently analyze an optical purity of charged compounds such as various amine derivatives, carboxylic acid derivatives, cyanohydrin derivatives, and charged metal complexes by $^1$H NMR spectroscopy.

BACKGROUND

Numerous compounds representing a physiological activity have chirality, and thus, are optically active, and it is known in the art that in many cases, two optical isomers in an enantiomeric relationship with each other represent different physiological activities from each other in a human body. In the past, these compounds were commercialized as a racemic mixture form, but nowadays, since a more selective activity is required, technique to separate two enantiomers forming a racemic mixture, and to measure an optical purity of an optically active compound is significantly needed.

Such a difference of the physiological activity is shown as a pharmacological effect in chiral medicine, and thus, more important. Therefore, there is needed the development of technique to separate an optically pure optical isomer by an asymmetric synthesis or optical resolution, and to accurately measure an optical purity, in the course of the development of new medicines.

The separation of the optical isomers includes all methods of separating racemates into pure optical isomers (optical resolution), and of classifying two optical isomers (measurement of optical purity).

As the method for measuring the optical purity of the compound having chirality, chromatographic methods such as gas chromatography and high performance liquid chromatography (HPLC) have been developed. Particularly, the Proton nuclear magnetic resonance ($^1$H-NMR) spectroscopy has received recent attention, for the reasons that an NMR instrument is widespread, as well as an analyte may be recovered, and also since an experiment in a solution state is possible with a small amount of a sample, analysis of both solid and liquid samples is possible. In a method of measuring an optical purity using NMR, the optical purity may be determined by converting a chiral analyte to two diastereomeric compounds using a chiral derivatizing agent (CDA), a chiral lanthanide shift reagent (CLSR), a chiral solvating agent (CSA), or the like, and carrying out analysis through NMR.

Among such methods, a chiral derivatizing agent method has disadvantages in that a derivatization process should be carried out once, and a functional group capable of being derivatized should be present, and a chiral lanthanide shift reagent method has a disadvantage in that a line broadening effect in a spectrum occurs. However, a chiral solvating agent has an advantage in that a non-destructive analysis is directly carried out in an NMR tube so that peak separation of a diastereomeric pairs may be seen, thereby conveniently showing an optical activity, and two diastereomers in an $^1$H NMR spectrum represent different chemical shifts (δ) from each other, and the optical purity of a chiral compound may be determined using the difference between the integrated values thereof.

Until now, though various chiral solvating agents have been developed, most of them may be used in the measurement of the optical purity of only specific chiral analytes, and thus, they are difficult to be applied to the measurement of the optical purity of a wider range of chiral analytes.

Related Art Document (Patent Document 1) Korean Patent Laid-Open Publication No. 1998-067965

(Patent Document 2) Korean Patent Registration No. 0170925

(Non-patent Document 1) J. Org. Chem. 1969, 34, 2543

(Non-patent Document 2) Angew. Chem. Int. Ed. 49, 7955-7957 (2010)

(Non-patent Document 3) Acc. Chem. Res. 46, 2635-2644 (2013)

SUMMARY

The present inventors intended to develop a chiral solvating agent for simply measuring an optical purity of chiral compounds, the optical purity being regarded as being difficult to be measured with a conventional chromatography method, by $^1$H NMR spectroscopy.

An embodiment of the present invention is directed to providing a novel ligand, and a metal complex including the same.

Another embodiment of the present invention is directed to providing a method of measuring an optical purity of various chiral compounds by $^1$H NMR spectroscopy, using the metal complex as a chiral solvating agent.

The present invention relates to a novel ligand, a chiral metal complex including the ligand, and a use of the chiral metal complex for analyzing chirality of a charged compound by $^1$H NMR spectroscopy. The chiral metal complex of the present invention may be used as a chiral solvating agent to conveniently analyze an optical purity of charged compounds such as various amine derivatives, carboxylic acid derivatives, cyanohydrin derivatives, and charged metal complexes by $^1$H NMR spectroscopy.

Hereinafter, the present invention will be described in detail.

The technical and scientific terms used herein have, unless otherwise defined, the meaning commonly understood by those of ordinary skill in the art. Further, repeated description of the same technical structure and operation as the prior art will be omitted.

In one general aspect, a $N_2O_2$ ligand is represented by following Chemical Formula 1:

[Chemical Formula 1]

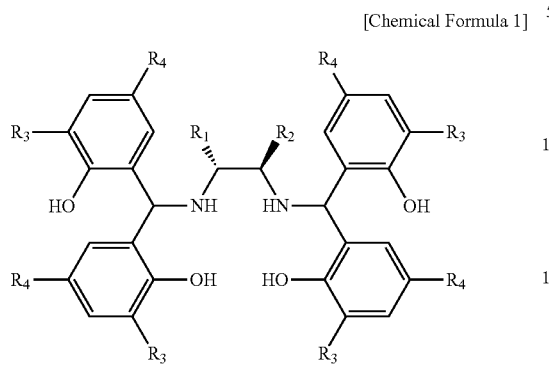

Wherein $R_1$ and $R_2$ are independently of each other (C1-C10) alkyl or (C6-C20) aryl, or $R_1$ and $R_2$ are linked via (C2-C6) alkylene to form a cycloaliphatic ring; and $R_3$ and $R_4$ are independently of each other hydrogen, (C1-C10) alkyl, (C6-C20) aryl, or halogen.

The term used herein, 'alkyl' refers to a monovalent straight-chain or branched-chain saturated hydrocarbon radical consisting of only carbon and hydrogen atoms, and an example of the alkyl radical includes methyl, ethyl, propyl, isopropyl, butyl, isobutyl, t-butyl, pentyl, hexyl, octyl, dodecyl, or the like, but not limited thereto.

The term used herein, 'aryl' refers to an organic radical derived from aromatic hydrocarbon by removal of one hydrogen, including a monocyclic or fused ring system containing suitably 4 to 7, preferably 5 or 6 ring atoms in each ring, and even a form in which a plurality of aryls are linked by a single bond. A specific example thereof includes phenyl, naphthyl, biphenyl, anthryl, indenyl, fluorenyl, or the like, but not limited thereto.

In an exemplary embodiment of the present invention, in the Chemical Formula 1, $R_1$ and $R_2$ may be independently of each other methyl, ethyl, propyl, butyl, pentyl, hexyl, phenyl, biphenyl, naphthyl or anthryl, or $R_1$ and $R_2$ may be linked via (C3-C4) alkylene to form a cycloaliphatic ring; and $R_3$ and $R_4$ may be independently of each other hydrogen, methyl, ethyl, propyl, butyl, pentyl, hexyl, phenyl, biphenyl, naphthyl, anthryl, chloro, bromo or fluoro.

In an exemplary embodiment of the present invention, the ligand of the Chemical Formula 1 may be selected from the following structures, but not limited thereto:

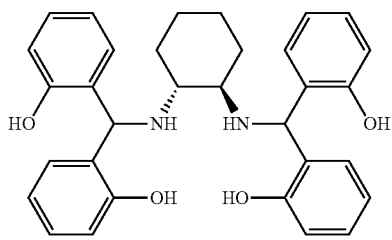

-continued

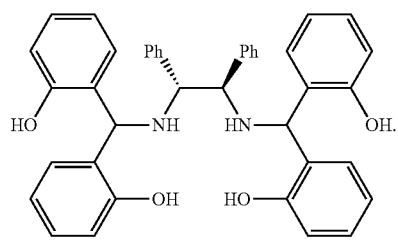

In an exemplary embodiment of the present invention, the ligand of the Chemical Formula 1 is efficiently prepared by imination and reducing amination reactions between (A) a chiral 1,2-diamine derivative and (B) a 2,2'-dihydroxybenzophenone derivative.

More specifically, the ligand of the Chemical Formula 1 is prepared through the following steps, as shown in following Reaction Formula 1:

1) Reacting a chiral 1,2-diamine derivative (Chemical Formula A) and a 2,2'-dihydroxybenzopphenone derivative (Chemical Formula B) to prepare a diimine compound (Chemical formula S); and 2) Reducing the diimine compound (Chemical Formula S) to prepare a ligand in the form of secondary amine (Chemical Formula 1).

[Reaction Formula 1]

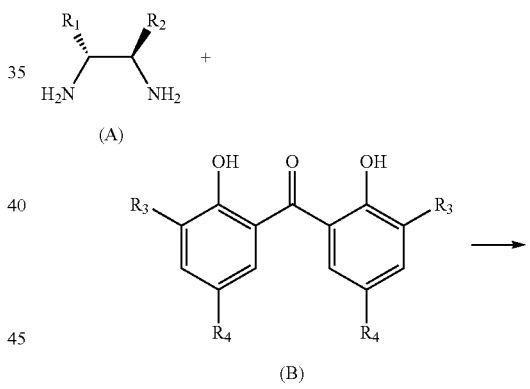

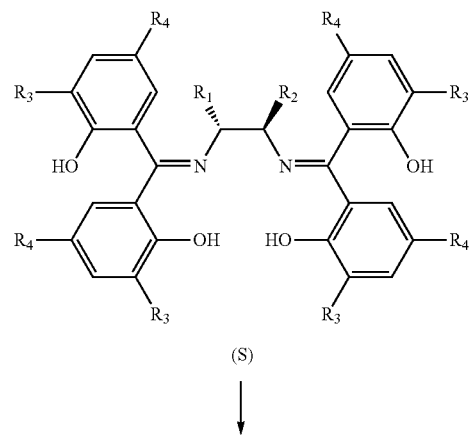

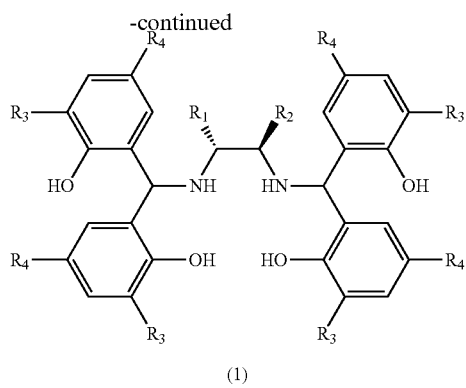

(1)

Wherein $R_1$ and $R_2$ are independently of each other (C1-C10) alkyl or (C6-C20) aryl, or $R_1$ and $R_2$ are linked via (C2-C6) alkylene to form a cycloaliphatic ring; and $R_3$ and $R_4$ are independently of each other hydrogen, (C1-C10) alkyl, (C6-C20) aryl or halogen.

A chiral 1,2-diamine derivative (Chemical Formula A) and a 2,2'-dihydroxybenzophenone derivative (Chemical Formula B) are reacted to produce a diimine compound (Chemical Formula S). The 2,2'-dihydroxybenzophenone derivative (Chemical Formula B) is used in excess of 2 equivalents or more relative to the chiral 1,2-diamine derivative (Chemical Formula A), preferably used at 2 to 10 equivalents relative to 1 equivalent of the chiral 1,2-diamine derivative (Chemical Formula A). The imination reaction may be carried out at a typical reaction temperature, preferably at 20 to 60° C.

The diimine compound (Chemical Formula S) may be prepared under an organic solvent or also under a neat condition, and it is not necessary to limit the organic solvent, as long as it dissolves the reactants. Under the 'neat' condition, the imine formation is carried out by mixing the chiral 1,2-diamine derivative (Chemical Formula A) and the 2,2'-dihydroxybenzophenone derivative (Chemical Formula B), without using the organic solvent. It is preferred that the solvent of the reaction is an inert solvent selected from the group consisting of methanol, ethanol, isopropanol, butanol, acetone, ethyl acetate, acetonitrile, isopropyl ether, methylethylketone, methylene chloride, dichlorobenzene, chlorobenzene, dichloroethane, tetrahydrofuran, toluene, benzene, xylene, mesitylene, dimethylformamide, dimethylsulfoxide and the like, considering the solubility of the reactants and the ease of removal thereof, and it is more preferred to use methanol, ethanol or a mixed solvent thereof.

The thus-produced diimine compound (Chemical Formula S) may be used in the next reaction without separation, purification, and an additional purification process, or may be subjected to a purification process, if necessary.

The produced diimine compound (Chemical Formula S) is reduced using a reducing agent to prepare a ligand in the form of secondary amine (Chemical formula 1). As the reducing agent, metal hydrides, preferably one or more selected from the group consisting of $NaBH_4$, $NaBH(OAc)_3$, $NaBH_2(OAc)_2$, $NaBH_3OAc$, $NaBH_3CN$, $KBH_4$, $KBH(OAc)$, $LiAlH_4$, $B_2H_6$ and DIBAL-H (diisobutylaluminium hydride), more preferably $NaBH_4$ may be used. The content of the reducing agent is not limited, however, used in an equal or excess amount relative to the diimine compound (Chemical Formula S), and it is preferred to use 1 to 10 equivalents, preferably 3 to 10 equivalents, more preferably 5 to 10 equivalents relative to 1 equivalent of the diimine compound (Chemical Formula S). The reduction reaction may be carried out at a typical reaction temperature, preferably at 20 to 40° C.

The ligand in the form of secondary amine (Chemical Formula 1) may be prepared under an organic solvent, and it is not necessary to limit the organic solvent, as long as it dissolves the reactants. It is preferred that the solvent of the reaction is an inert solvent selected from the group consisting of methanol, ethanol, isopropanol, acetone, ethyl acetate, acetonitrile, isopropyl ether, methylethylketone, methylene chloride, dichlorobenzene, chlorobenzene, dichloroethane, tetrahydrofuran, toluene, benzene and xylene, considering the solubility of the reactants and the ease of removal thereof, and it is more preferred to use methanol, ethanol or a mixed solvent thereof.

All of the reactions are completed after confirming that starting materials are all consumed, by TLC and the like. When the reaction is completed, the solvent is distilled under reduced pressure, if necessary, and then the desired material may be separated and purified by a typical method such as filtration, column chromatography, recrystallization and the like.

In another general aspect, a chiral metal complex including the $N_2O_2$ ligand of the Chemical Formula 1 is represented by following Chemical Formula 2:

[Chemical Formula 2]

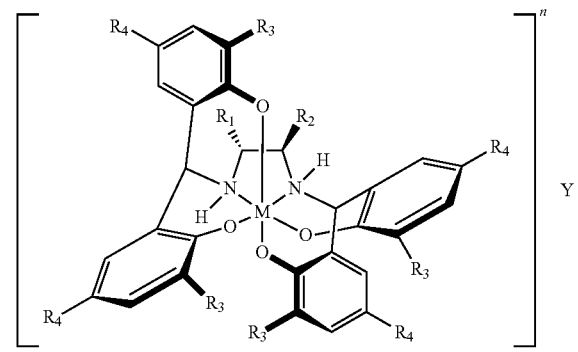

wherein $R_1$ and $R_2$ are independently of each other (C1-C10) alkyl or (C6-C20) aryl, or $R_1$ and $R_2$ are linked via (C2-C6) alkylene to form a cycloaliphatic ring;

$R_3$ and $R_4$ are independently of each other hydrogen, (C1-C10) alkyl, (C6-C20) aryl, or halogen;

when M is $Al^{3+}$ or $Sc^{3+}$, n is −1, and Y is $H^+$, $Li^+$, $Na^+$, $K^+$, $Ag^+$, $Cs^+$, $NR_4^+$, ½ $Mg^{2+}$, ½ $Ca^{2+}$, ½ $Zn^{2+}$ or ⅓ $Al^{3+}$; and When M is $Ti^{4+}$, n is 0, and Y does not exist.

The chiral metal complex of the Chemical Formula 2 of the present invention is a chiral octahedral complex having a Δ or Λ configuration at a metal center due to the binding of the ligand of the Chemical formula 1, and it is possible to stereoselectively control Δ or Λ chirality at the metal center.

The chiral metal complex of the Chemical Formula 2 of the present invention may have the number of the ligand of the Chemical Formula 1 varying with the oxidation number of Y, and when the oxidation number of Y is +2, the number of the ligand of the Chemical Formula 1 is 2, and when the oxidation number of Y is +3, the number of ligand of the Chemical Formula 1 is 3.

Specifically, in the chiral metal complex of the Chemical Formula 2 according to an exemplary embodiment of the present invention, $R_1$ and $R_2$ may be independently of each other methyl, ethyl, propyl, butyl, pentyl, hexyl, phenyl, biphenyl, naphthyl or anthryl, or $R_1$ and $R_2$ may be linked via (C3-C4) alkylene to form a cycloaliphatic ring; $R_3$ and $R_4$ may be independently of each other hydrogen, methyl, ethyl, propyl, butyl, pentyl, hexyl, phenyl, biphenyl, naphthyl, anthryl, chloro, bromo or fluoro; M may be $Al^{3+}$, $Sc^{3+}$ or $Ti^{4+}$; n may be 0 or −1; and Y may not exist, or may be $H^+$ or $Na^{30}$.

More preferably, in the chiral metal complex of the Chemical Formula 2 according to an exemplary embodiment of the present invention, $R_1$ and $R_2$ may be independently of each other alkyl(C1-C10), phenyl, biphenyl, naphthyl or anthryl, or $R_1$ and $R_2$ may be linked via (C3-C4) alkylene to form a cycloaliphatic ring; $R_3$ and $R_4$ may be independently of each other hydrogen; M may be $Al^{3+}$, $Sc^{3+}$ or $Ti^{4+}$; n may be 0 or −1; and Y may not exist, or may be $H^+$ or $Na^+$.

More specifically, the chiral metal complex of the Chemical Formula 2 according to an exemplary embodiment of the present invention may be selected from the following structures, but not limited thereto:

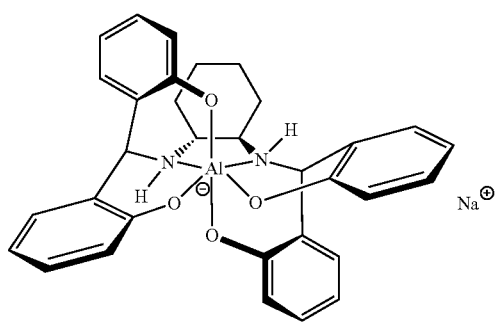

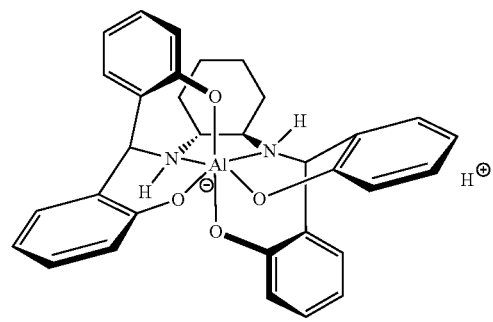

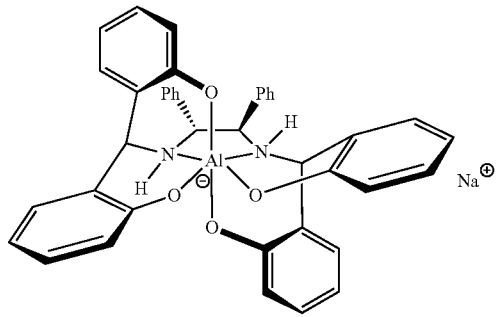

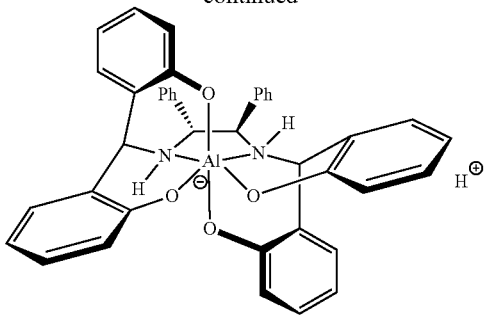

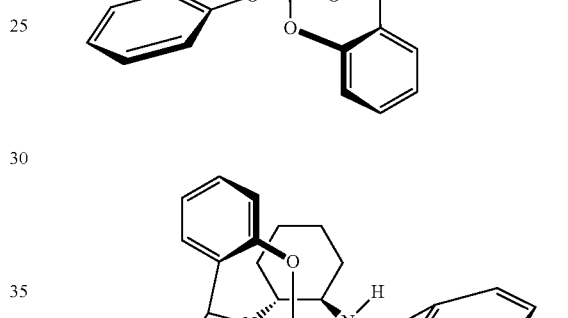

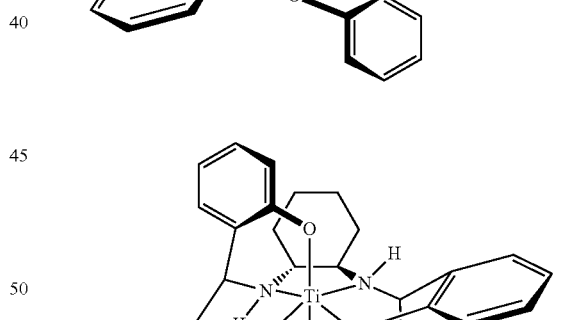

In an exemplary embodiment of the present invention, when the central metal M of the chiral metal complex of the Chemical Formula 2 is $Al^3$ or $Sc^{3+}$, the ligand of the Chemical Formula 1, the metal salt of the Chemical Formula 3-1, and the base of the Chemical Formula 4 are reacted to produce the chiral metal complex of the Chemical Formula 2-1, or the chiral metal complex of the Chemical Formula 2-1 is subjected to acid treatment to prepare the chiral metal complex of the Chemical Formula 2-2, as shown in the following Reaction Formula 2:

[Reaction Formula 2]

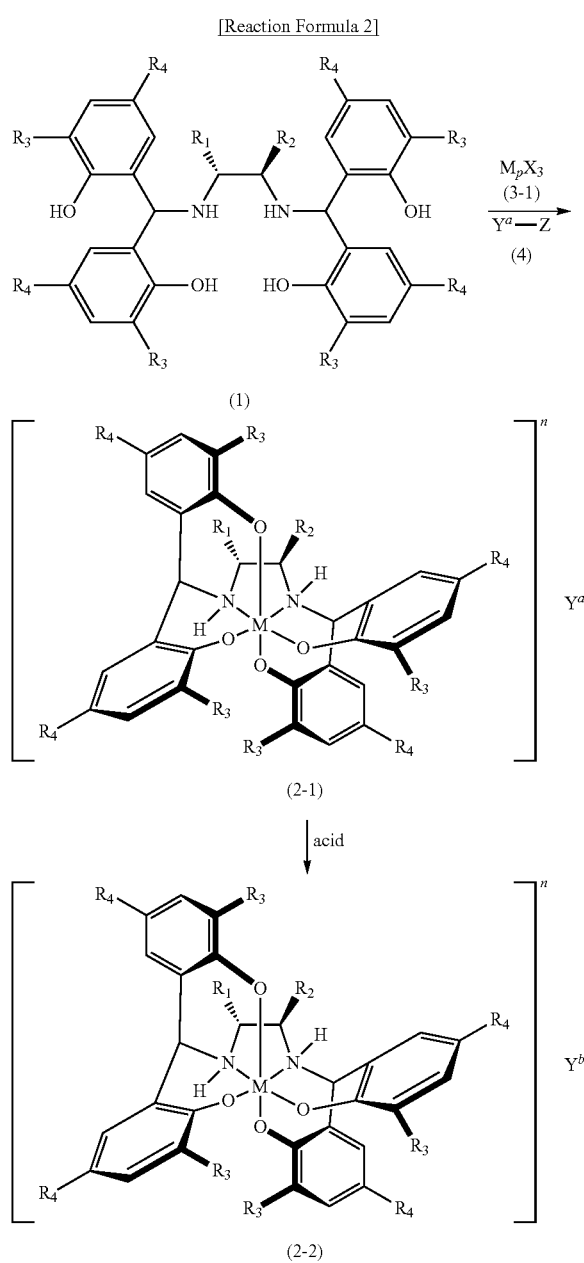

wherein $R_1$ and $R_2$ are independently of each other (C1-C10) alkyl or (C6-C20) aryl, or $R_1$ and $R_2$ are linked via (C2-C6) alkylene to form a cycloaliphatic ring;

$R_3$ and $R_4$ are independently of each other hydrogen, (C1-C10) alkyl, (C6-C20) aryl, or halogen;

M is $Al^{3+}$ or $Sc^{3+}$;

when p is an integer of 1, X is a monovalent anion, for example, halogen, acetylacetonato (acac), hydroxy, alkoxy, triflate, nitro, acetoxy or perchlorate;

when p is an integer of 2, X is a divalent anion, for example, sulfate;

n is an integer of 1;

$Y^a$ is $Li^+$, $Na^+$, $K^+$, $Ag^+$, $Cs^+$, $NR_4^+$, ½ $Mg^{2+}$, ½ $Ca^{2+}$, ½ $Zn^{2+}$ or ⅓ $Al^{3+}$;

z is $OH^-$ or $H^-$; and $Y^b$ is $H^{3O}$.

The chiral metal complex (Chemical Formula 2-1) is prepared by reacting the ligand in the form of secondary amine (Chemical Formula 1) with a base (Chemical Formula 4) and a metal salt (Chemical Formula 3-1). It is preferred that as the base (Chemical Formula 4), one or more selected from the group consisting of LiOH, NaOH, KOH, $NMe_4OH$, NaH and KH are used. The content of the base (Chemical Formula 4) is not limited, but the base is used in 4 to 6 equivalents relative to the ligand in the form of secondary amine (Chemical Formula 1). The metal complexation reaction may be carried out at a typical reaction temperature, preferably at 20° C. to 80° C. The metal salt (Chemical Formula 3-1) may be selected from the group consisting of $AlF_3$, $AlCl_3$, $AlBr_3$, $Al(acac)_3$, $Al_2(SO_4)_3$, $Al(OH)_3$, $Al(OEt)_3$, $Al(OiPr)_3$, $ScF_3$, $ScCl_3$, $ScBr_3$, $ScI_3$, $Sc(OTf)_3$, $Sc(NO_3)_3$, $Sc(OiPr)_3$, $Sc(OAc)_3$, $Sc(ClO_4)_3$ and $Sc_2(SO_4)_3$.

The chiral metal complex may be prepared under an organic solvent, and it is not necessary to limit the organic solvent, as long as it dissolves the reactants. It is preferred that the solvent of the reaction is an inert solvent selected from the group consisting of methanol, ethanol, isopropanol, butanol, acetone, ethyl acetate, acetonitrile, isopropyl ether, methylethylketone, methylene chloride, dichlorobenzene, chlorobenzene, dichloroethane, tetrahydrofuran, toluene, benzene, xylene, mesitylene, dimethylformamide, dimethylsulfoxide and the like, considering the solubility of the reactants and the ease of removal thereof, and it is more preferred to use methanol.

Further, the chiral metal complex (Chemical Formula 2-2) wherein $Y^b$ is $H^+$ is prepared by subjecting the chiral metal complex (Chemical Formula 2-1) with acid treatment, and any common acid may be used. Specifically, the available acid may be exemplified by trifluoroacetic acid (TFA), p-toluenesulfonic acid (p-TsOH), benzenesulfonic acid ($PhSO_3H$), acetic acid, phosphoric acid ($H_3PO_4$), hydrogen chloride (HCl), hydrogen bromide (HBr), sulfuric acid ($H_2SO_4$), and nitric acid ($HNO_3$), but not limited thereto.

The thus-produced chiral metal complex may be used in the next reaction without separation, purification, and an additional purification process, or may be subjected to a purification process, if necessary.

Further, in an exemplary embodiment of the present invention, when the central metal M of the chiral metal complex of the Chemical formula 2 is $Ti^{4+}$, the ligand of the Chemical Formula 1 and the titanium salt of the Chemical Formula 3-2 are reacted to produce the chiral metal complex of the Chemical Formula 2-3, as shown in following Reaction Formula 3:

[Reaction Formula 3]

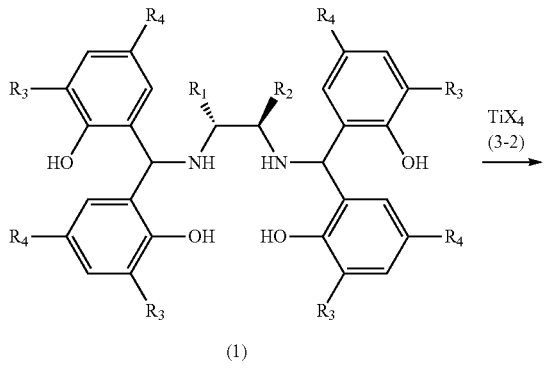

-continued

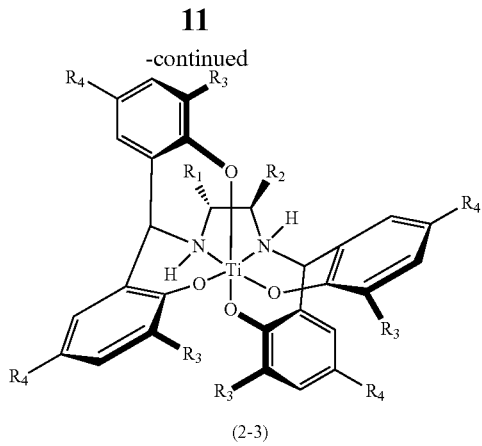

(2-3)

wherein

R$_1$ and R$_2$ are independently of each other (C1-C10) alkyl or (C6-C20) aryl, or R$_1$ and R$_2$ are linked via (C2-C6) alkylene to form a cycloaliphatic ring;

R$_3$ and R$_4$ are independently of each other hydrogen, (C1-C10) alkyl, (C6-C20) aryl, or halogen; and X is a monovalent anion, for example, halogen, acetylacetonato (acac), hydroxy, alkoxy, triflate, nitro, acetoxy or perchlorate.

The chiral metal complex (Chemical Formula 2-3) is prepared by reacting the ligand in the form of secondary amine (Chemical Formula 1) and the titanium salt (Chemical Formula 3-2). The metal complexation reaction may be carried out at a typical reaction temperature, preferably at 20° C. to 80° C. The titanium salt (Chemical Formula 3-2) may be selected from the group consisting of TiCl$_4$, TiBr$_4$, Ti(OEt)$_4$, Ti(OiPr)$_4$ and Ti(OtBu)$_4$.

The chiral metal complex may be prepared under an organic solvent, and it is not necessary to limit the organic solvent, as long as it dissolves the reactants. It is preferred that the solvent of the reaction is an inert solvent selected from the group consisting of methanol, ethanol, isopropanol, butanol, acetone, ethyl acetate, acetonitrile, isopropyl ether, methylethylketone, methylene chloride, dichlorobenzene, chlorobenzene, dichloroethane, tetrahydrofuran, toluene, benzene, xylene, mesitylene, dimethylformamide, dimethylsulfoxide and the like, considering the solubility of the reactants and the ease of removal thereof, and it is more preferred to use methanol.

The thus-produced chiral metal complex may be used in the next reaction without separation, purification, and an additional purification process, or may be subjected to a purification process, if necessary.

In still another general aspect, a use of a chiral metal complex of the Chemical Formula 2 is for analyzing chirality of a charged compound by spectroscopy, and more specifically, a chiral metal complex of the Chemical Formula 2 is used as a chiral solvating agent to provide a method of measuring an optical purity of various chiral compounds by $^1$H NMR spectroscopy.

In an exemplary embodiment of the present invention, the spectroscopy is nuclear magnetic resonance (NMR) spectroscopy, and a method of measuring an optical purity of a chiral analyte using $^1$H NMR is specifically as follows.

An analyte for measuring the optical purity thereof is dissolved in an NMR solvent, and placed in an NMR tube to measure NMR, thereafter, the analyte and the chiral metal complex of the present invention (Chemical Formula 2) are mixed and dissolved in the same NMR solvent as the above, and placed in an NMR tube to measure NMR. As the chiral metal complex of the present invention is added, diastereomeric non-equilibrium appears, and the peak shift values of two isomers are shown differently, and the classified two peaks are integrated, thereby measuring the optical purity of the analyte.

The analyte for measuring the optical purity thereof is a charged compound such as various amine derivatives, carboxylic acid derivatives, cyanohydrin derivatives and charged metal complexes, and includes even a commercial racemic drug which is difficult to be subjected to chromatography analysis due to high polarity and low solubility in an organic solvent.

The NMR solvent which is an organic solvent capable of dissolving the analyte and the chiral metal complex may be used in an NMR analysis, and include a polar or a non-polar organic solvent substituted by deuterium. The polar solvent may be exemplified by $CD_3CN$, $CD_3OD$, $(CD_3)_2CO_3$ $(CD_3)_2SO$ or $D_2O$, and the non-polar solvent may be exemplified by $CDCl_3$, $C_6D_6$ or $CD_2Cl_2$.

It was confirmed that as an added amount of the chiral metal complex of the present invention (Chemical Formula 2) is increased, the peak separation distance of the analyte is getting wider, and the chiral metal complex of the present invention (Chemical Formula 2) is added in 0.1 equivalent or more, preferably in 0.5 to 10 equivalents relative to the analyte, but even in the case of being added in a small amount relative to the analyte, NMR peaks are sufficiently separated.

Traditionally only the non-polar solvent was used so that the range of the analyte was extremely limited, however, in the present invention, the polar solvent as well as the non-polar solvent may be used, and thus, even the analyte which has high polarity and was not able to be previously used as the analyte may be used.

Other features and aspects will be apparent from the following detailed description, the drawings, and the claims.

DETAILED DESCRIPTION OF EMBODIMENTS

Figure 1:
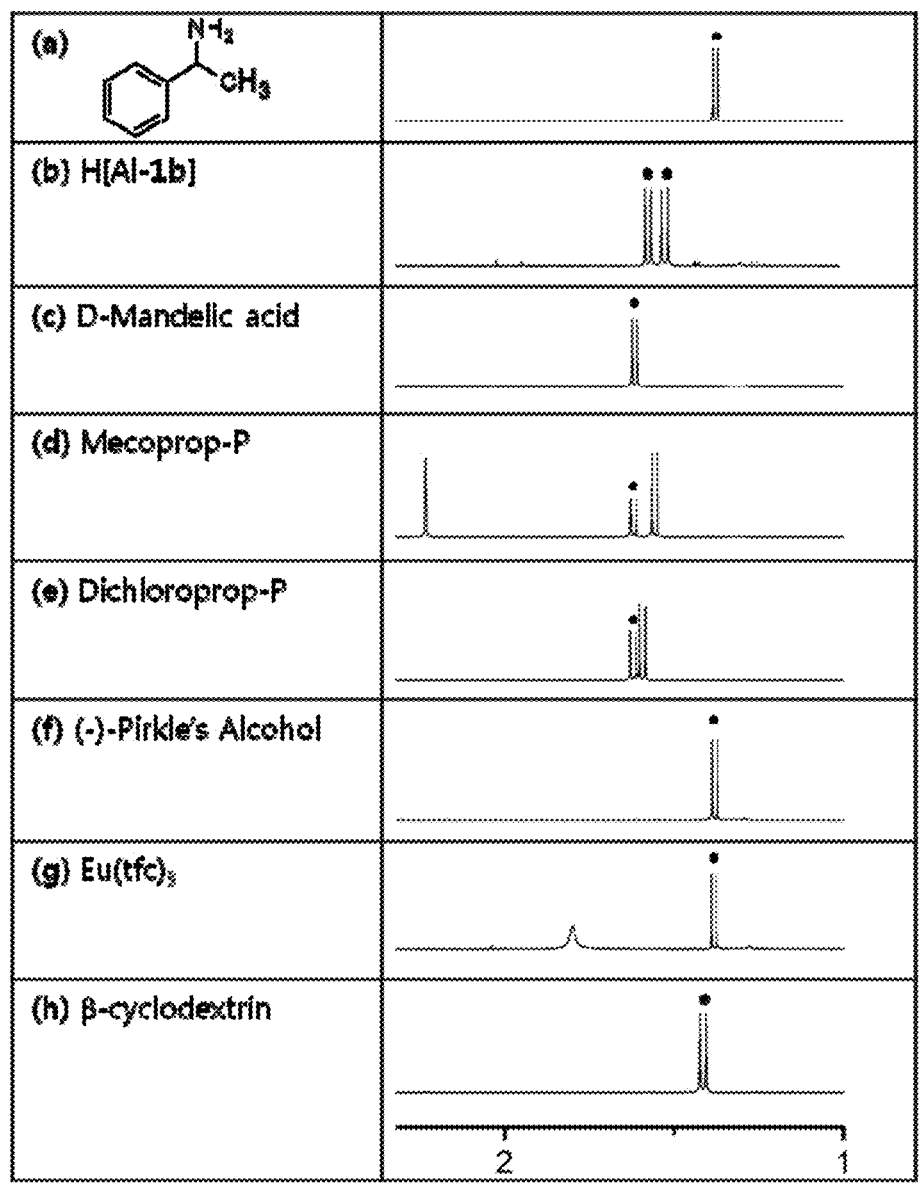
FIG. 1 is $^1$H NMR spectra of Example 9 and Comparative Examples 1 to 6.

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

Commercially available compounds were used without additional purification or drying. $^1$H NMR (400 MHz) and $^{13}$C NMR (100 MHz) spectra were obtained using a Bruker Ascend 400 spectrometer. HRMS (high-resolution mass spectra) was obtained using a Bruker Daltonik microTOF-QII spectrometer.

Example 1

Preparation of Ligand 1a

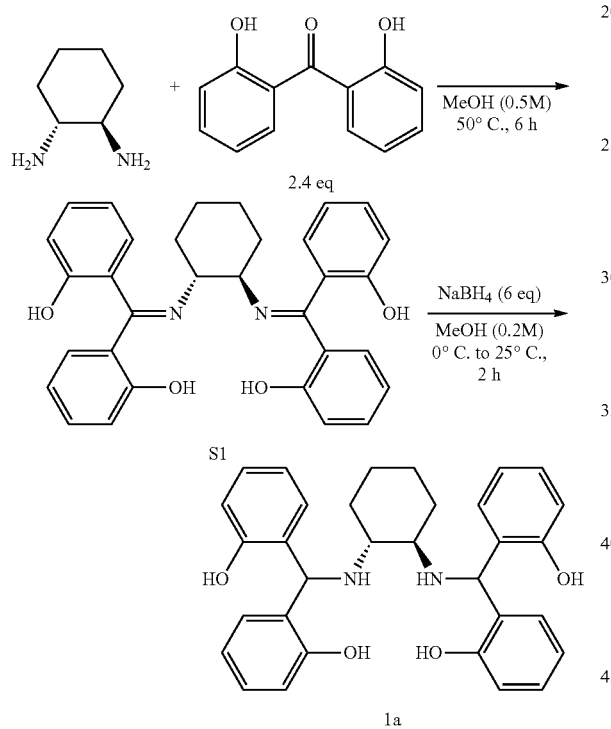

1a

Preparation of Compound S1

(R,R)-1,2-diaminocyclohexane (1.14 g, 10.0 mmol) and MeOH (20.0 mL) were mixed, and then 2,2'-dihydroxybenzophenone (5.14 g, 24.0 mmol) was added thereto while stirring, and the stirring was continued at 50° C. for 6 hours. The reaction mixture was filtered, and the separated solid was washed with ether, and then dried in vacuo, thereby obtaining title compound S1 as a yellow solid (4.41 g, 87%).

$^1$H NMR (400 MHz, DMSO-d6) δ 15.55-15.27 (br, 2H), 9.81 (br, 2H), 7.39-7.32 (m, 2H), 7.26-7.20 (m, 2H), 7.12-6.81 (m, 8H), 6.73-6.61 (m, 4H), 3.56-3.45 (m, 2H), 1.88-1.69 (m, 2H), 1.58 (br, 2H), 1.32 (br, 2H), 1.09 (br, 2H); $^{13}$C NMR (100 MHz, DMSO-d6) δ 171.5, 162.1, 154.0, 132.1, 130.7, 130.5, 128.5, 120.4, 119.5, 119.2, 117.5, 117.2, 115.8, 649.9, 30.9, 23.5; HRMS (EI m/z calcd for $C_{32}H_{30}N_2O_4$ [H]$^+$: 507.2278. found: 507.2314.

Preparation of Compound 1a

Compound S1 (2.53 g, 5.00 mmol) and MeOH (25.0 mL) were mixed, and then NaBH$_4$ (6 eq., 1.13 g, 30.0 mmol) was added portionwise at 0° C. while stirring, and the stirring was continued at 25° C. for 2 hours. All volatile residues were removed in vacuo, and then the reaction mixture was dissolved in EtOAc, and washed with brine. The organic layer was dried with MgSO$_4$, and filtered and concentrated. Purification by reslurrying (CHCl$_3$, 10.0 mL) gave title compound 1a as a white solid (1.66 g, 65%).

$^1$H NMR (400 MHz, DMSO-d6) δ 8.29 (br, 6H), 7.10-7.02 (m, 6H), 6.80-6.78 (m, 4H), 6.75-6.70 (m, 4H), 6.65 (td, J=7.5, 1.1 Hz, 2H), 5.36 (s, 2H), 2.45 (br, 2H), 2.02 (br, 2H), 1.56 (br, 2H), 1.16 (br, 4H); $^{13}$C NMR (100 MHz, DMSO-d6) δ 156.6, 155.8, 128.6, 128.2, 128.0, 127.9, 127.7, 126.7, 118.9, 118.5, 115.7, 115.5, 57.0, 55.5, 28.5, 22.9; HRMS (EI) m/z calcd for $C_{32}H_{34}N_2O_4$[H]$^+$: 511.2591. found: 511.2607.

Example 2

Preparation of Ligand 1b

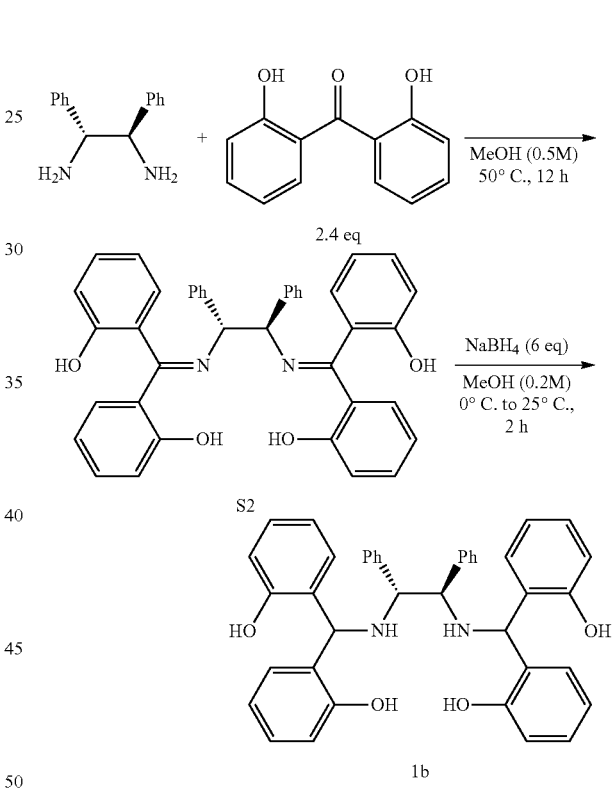

1b

Preparation of Compound S2

(R,R)-1,2-diphenylethylenediamine (2.12 g, 10.0 mmol) and MeOH (20.0 mL) were mixed, and then 2,2'-dihydroxybenzophenone (5.14 g, 24.0 mmol) was added thereto while stirring, and the stirring was continued at 50° C. for 12 hours. The reaction mixture was filtered, and the separated solid was washed with ether, and then dried in vacuo, thereby obtaining title compound S2 as a yellow solid (5.51 g, 91%).

$^1$H NMR (400 MHz, DMSO-d6) δ 15.39-15.32 (br, 2H), 9.40 (br, 2H), 7.31-7.22 (m, 4H), 7.18-6.80 (m, 14H), 6.74-6.50 (m, 6H), 6.21-6.08 (m, 2H), 4.95-4.84 (m, 2H); $^{13}$C NMR (100 MHz, DMSO-d6) δ 172.8, 161.9, 154.0, 139.8, 132.4, 131.1, 130.5, 128.0, 127.7, 127.0, 119.8, 119.5, 118.6, 117.7, 117.5, 117.2, 115.3, 71.8; HRMS (EI) m/z calcd for $C_{40}H_{32}N_2O_4$ [H]$^+$: 605.2435. found: 605.2476.

Preparation of Compound 1b

Compound S2 (3.02 g, 5 mmol) and MeOH (25.0 mL) were mixed, and then NaBH₄ (6 eq., 1.13 g, 30.0 mmol) was added portionwise at 0° C. while stirring, and the stirring was continued at 25° C. for 2 hours. All volatile residues were removed in vacuo, and then the reaction mixture was dissolved in EtOAc, and washed with brine. The organic layer was dried with MgSO₄, and filtered and concentrated. Purification by reslurrying (CHCl₃, 10.0 mL) gave title compound 1b as a white solid (2.47 g, 81%).

$^1$H NMR (400 MHz, DMSO-d6) δ 10.07 (br, 4H), 7.16-7.08 (m, 8H), 7.01-6.92 (m, 8H), 6.77 (dd, J=8.1, 1.0 Hz, 2H), 6.75-6.71 (m, 4H), 6.69 (dd, J=8.0, 1.1 Hz, 2H), 6.60 (td, J=7.5, 1.2 Hz, 2H), 4.94 (s, 2H), 3.79 (s, 2H); $^{13}$C NMR (100 MHz, DMSO-d6) δ 155.9, 155.8, 139.6, 128.9, 128.2, 128.1, 128.0, 128.0, 128.0, 127.8, 127.7, 127.0, 125.8, 118.9, 118.4, 115.6, 115.5, 65.2, 55.5; HRMS (EI) m/z calcd for $C_{40}H_{36}N_2O_4[H]^+$: 609.2748. found: 605.2473.

Example 3

Preparation of Metal Complex Na[Al-1a]

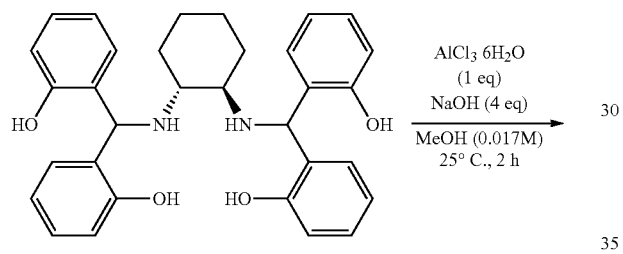

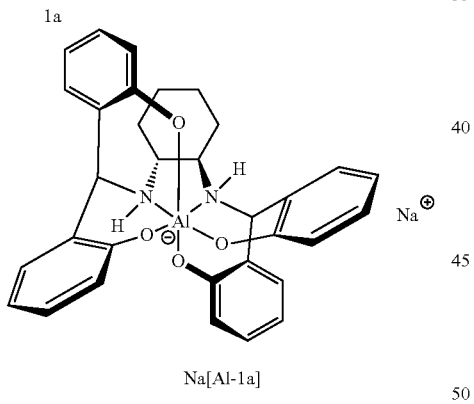

Na[Al-1a]

Compound 1a (511 mg, 1.00 mmol) and MeOH (20.0 mL) were mixed to prepare a solution of compound 1a. NaOH (160 mg, 4.00 mmol) and MeOH (40.0 mL) were mixed to prepare a NaOH solution. The NaOH solution and AlCl₃·6H₂O (241 mg, 1.00 mmol) were added to the solution of compound 1a, and stirred at 25° C. for 2 hours. The reaction mixture was concentrated under reduced pressure, dissolved in EtOAc, and washed with brine. The organic layer was dried with Na₂SO₄, filtered, and concentrated under reduced pressure to obtain title compound Na[Al-1a] as an off-white solid (559 mg, 99%).

$^1$H NMR (400 MHz, DMSO-d6) δ 7.08 (dd, J=7.5, 1.7 Hz, 2H), 6.95-6.86 (m, 4H), 6.78 (ddd, J=8.1, 7.1, 1.9 Hz, 2H), 6.62 (dd, J=8.1, 1.3 Hz, 2H), 6.38 (td, J=7.3, 1.3 Hz, 2H), 6.31 (dd, J=8.2, 1.2 Hz, 2H), 6.26 (td, J=7.2, 1.3 Hz, 2H), 4.87 (s, 2H), 3.77 (d, J=10.2 Hz, 2H), 2.48-2.41 (m, 2H), 2.23 (d, J=12.7 Hz, 2H), 1.65 (d, J=9.8 Hz, 2H), 1.27 (d, J=11.5 Hz, 2H), 1.01-0.90 (m, 2H); $^{13}$C NMR (100 MHz, DMSO-d6) δ 162.3, 161.8, 130.4, 129.2, 128.5, 127.8, 127.3, 124.9, 120.1, 120.1, 113.4, 113.0, 63.3, 55.8, 27.3, 24.1; HRMS (EI) m/z calcd for $C_{32}H_{30}AlN_2NaO_4[H]^+$: 557.1991. found: 557.2035.

Example 4

Preparation of Metal Complex H[Al-1a]

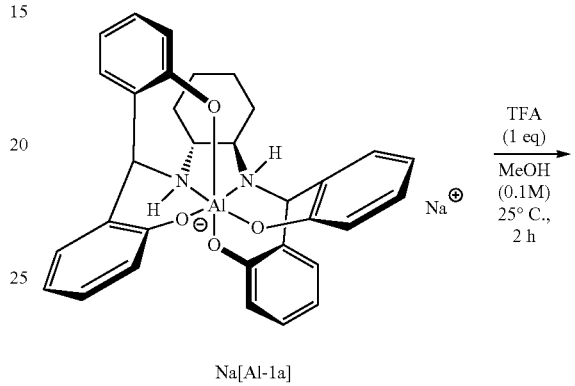

Na[Al-1a]

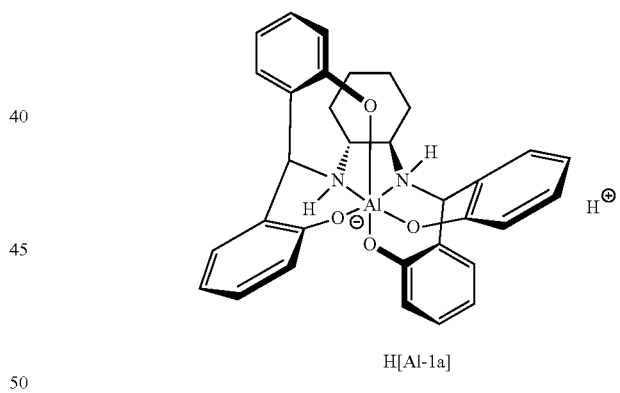

H[Al-1a]

Na[Al-1a] (278 mg, 0.500 mmol) and MeOH (5.00 mmol) were mixed, and then TFA (38.3 uL, 0.500 mmol) was added thereto, and stirred at 25° C. for 2 hours. The reaction mixture was dried, washed with cold MeOH, and then dried in vacuo to obtain title compound H[Al-1a] as an off-white solid (235 mg, 88%).

$^1$H NMR (400 MHz, DMSO-d6) δ 7.18-7.14 (m, 4H), 6.99-6.93 (m, 4H), 6.64 (d, J=8.0 Hz, 2H), 6.59-6.54 (m, 4H), 6.48 (t, J=7.2 Hz, 2H), 5.07 (s, 2H), 4.61 (br, 2H), 2.45-2.36 (m, 2H), 2.21 (d, J=13 Hz, 2H), 1.63 (d, J=9.4 Hz, 2H), 1.29 (d, J=7.8 Hz, 2H) 0.96-0.85 (m, 2H); $^{13}$C NMR (100 MHz, DMSO-d6) δ 160.9, 157.0, 130.0, 129.4, 129.3, 128.7, 128.3, 125.9, 120.2, 119.9, 117.5, 115.3, 62.9, 56.6, 27.2, 24.4; HRMS (EI) m/z calcd for $C_{32}H_{31}AlN_2O_4[Na]^+$: 557.1991. found: 557.1990.

Example 5

Preparation of Metal Complex Na[Al-1b]

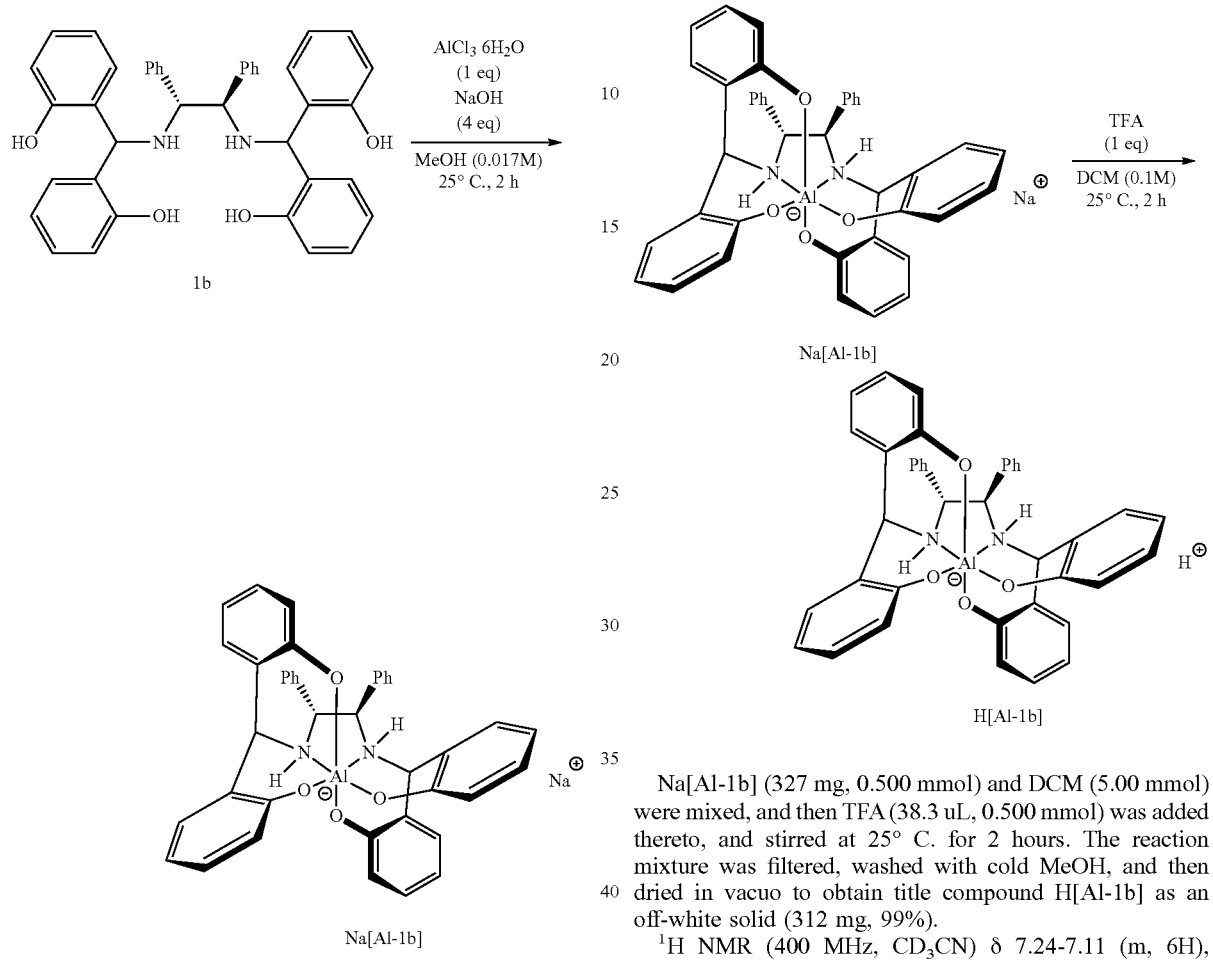

Compound 1b (609 mg, 1.00 mmol) and MeOH (20.0 mL) were mixed to prepare a solution of compound 1b. NaOH (160 mg, 4.00 mmol) and MeOH (40.0 mL) were mixed to prepare a NaOH solution. The NaOH solution and AlCl$_3$·6H$_2$O (241 mg, 1.00 mmol) were added to the solution of compound 1b, and stirred at 25° C. for 2 hours. The reaction mixture was concentrated under reduced pressure, dissolved in EtOAc, and washed with brine. The organic layer was dried with Na$_2$SO$_4$, filtered, and concentrated under reduced pressure to obtain title compound Na[Al-1b] as an off-white solid (648 mg, 99%).

$^1$H NMR (400 MHz, DMSO-d6) δ 7.21-7.14 (m, 6H), 6.94-6.89 (m, 4H), 6.86-6.84 (m, 4H), 6.76-6.73 (m, 4H), 6.65 (dd, J=8.2, 1.4 Hz, 2H) 6.49 (dd, J=8.2, 1.2 Hz, 2H) 6.34 (ddd, 15.1, 7.6, 1.1 Hz, 2H) 6.29 (td, J=7.3, 1.2 Hz, 2H), 4.31 (s, 2H), 4.14-4.07 (m, 2H), 3.88-3.83 (m, 2H); $^{13}$C NMR (100 MHz, DMSO-d6) δ 162.1, 161.6, 136.3, 129.3, 129.1, 128.7, 128.3, 128.2, 128.1, 127.9, 127.6, 124.2, 120.3, 120.2, 113.7, 113.6, 64.7, 62.4; HRMS (EI) m/z calcd for C$_{40}$H$_{32}$AlN$_2$NaO$_4$[H]$^+$: 655.2148. found: 655.2167.

Example 6

Preparation of Metal Complex H[Al-1a]

Na[Al-1b] (327 mg, 0.500 mmol) and DCM (5.00 mmol) were mixed, and then TFA (38.3 uL, 0.500 mmol) was added thereto, and stirred at 25° C. for 2 hours. The reaction mixture was filtered, washed with cold MeOH, and then dried in vacuo to obtain title compound H[Al-1b] as an off-white solid (312 mg, 99%).

$^1$H NMR (400 MHz, CD$_3$CN) δ 7.24-7.11 (m, 6H), 6.99-6.70 (m, 16H), 6.99-6.97 (m, 6H) 6.85-6.78 (m, 6H), 6.74-6.70 (m, 2H), 6.48-6.45 (m, 2H), 4.63 (br, 2H), 4.60 (d, J=1.8 Hz, 2H), 4.32-4.25 (m, 2H); $^{13}$C NMR (100 MHz, CD$_3$CN) δ 135.6, 130.6, 130.0, 129.9, 129.8, 129.8, 129.4, 129.3, 128.7, 125.0, 121.6, 120.4, 65.3, 64.1; HRMS (EI) m/z calcd for C$_{40}$H$_{33}$AlN$_2$O$_4$[Na]$^+$: 655.2148. found: 655.2180.

Example 7

Preparation of Metal Complex Na[Sc-1a]

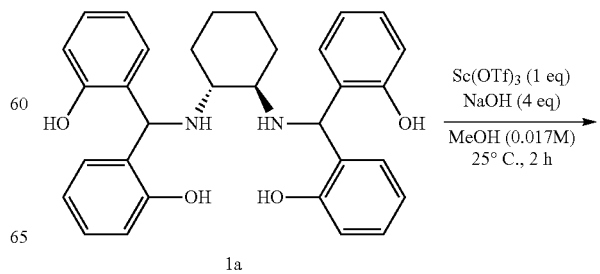

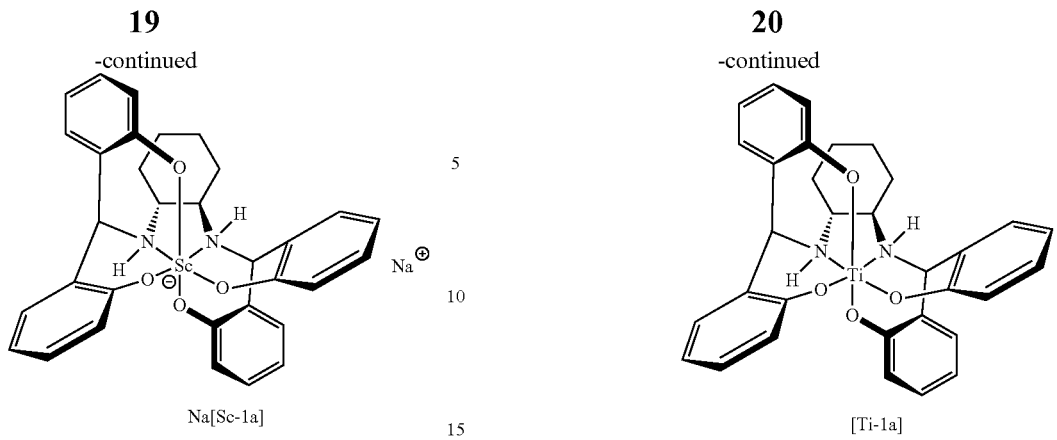

Na[Sc-1a]

[Ti-1a]

Compound 1a (511 mg, 1.00 mmol) and MeOH (20.0 mL) were mixed to prepare a solution of compound 1a. NaOH (160 mg, 4.00 mmol) and MeOH (40.0 mL) were mixed to prepare a NaOH solution. The NaOH solution and Sc(OTf)$_3$ (492 mg, 1.00 mmol) were added to the solution of compound 1a, and stirred at 25° C. for 2 hours. The reaction mixture was concentrated under reduced pressure, dissolved in EtOAc, and washed with brine. The organic layer was dried with Na$_2$SO$_4$, filtered, and concentrated under reduced pressure to obtain title compound Na[Sc-1a] as an off-white solid (568 mg, 99%).

$^1$H NMR (400 MHz, DMSO-d6) δ 7.11 (d, J=6.2 Hz, 2H), 6.91 (d, J=7.4 Hz, 2H), 6.86 (t, J=7.5 Hz, 2H), 6.75 (t, J=7.5 Hz, 2H), 6.32 (t, J=7.3 Hz, 2H), 6.28 (d, J=8.1 Hz, 2H), 6.23-6.19 (m, 4H), 4.91 (s, 2H), 3.44 (d, J=9.4 Hz, 2H), 2.53-2.57 (m, 2H), 2.33 (d, J=10.9 Hz, 2H), 1.63 (d, J=7.7 Hz, 2H), 1.25-1.15 (m, 2H), 0.99-0.88 (m, 2H).

Example 8

Preparation of Metal Complex [Ti-1a]

Compound 1a (511 mg, 1.00 mmol) and methanol (10.0 mL) were mixed to prepare a solution of compound 1a. Ti(OiPr)$_4$ (0.296 mL, 1.00 mmol) was added to the solution of compound 1a, and stirred at 25° C. for 2 hours. The reaction mixture was filtered, and then washed with methanol. The solid compound was dried to obtain title compound [Ti-1a] as a yellow solid (477 mg, 86%).

$^1$H NMR (400 MHz, DMSO-d6) δ 7.46 (dd, J=7.6, 1.7 Hz, 2H), 7.22 (dd, J=7.7, 1.8 Hz, 2H), 7.10 (ddd, J=8.0, 7.3, 1.7 Hz, 2H), 6.97 (ddd, J=8.1, 7.2, 1.8 Hz, 2H) 6.76 (td, J=7.4, 1.2 Hz, 2H), 6.58 (td, J=7.4, 1.2 Hz, 2H) 6.52 (dd, J=8.0, 1.2 Hz, 2H), 6.33 (dd, J=8.1, 1.2 Hz, 2H) 6.07 (d, J=8.2 Hz, 2H), 5.36-5.28 (m, 2H), 2.69-2.79 (m, 2H), 2.32-2.28 (m, 2H), 1.65-1.67 (m, 2H), 1.48-1.40 (m, 2H), 0.95-0.84 (m, 2H).

Example 9 and Comparative Examples 1 to 6

Measurement of Optical Purity of Rac-1-Phenylethylamine by $^1$H NMR Using Chiral Solvating Agents As shown in following Table 1, various chiral solvating agents and rac-1-phenylethylamine were dissolved in an NMR solvent at 25° C., and then measurement of $^1$H NMR spectra was carried out, thereby confirming whether two enantiomers are classified, and the results are illustrated in FIG. 1. (a) in FIG. 1 is $^1$H NMR of a methyl group of rac-1-phenylethylamine in CD$_3$OD.

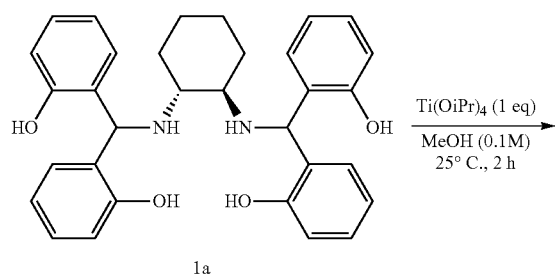

1a

TABLE 1

| | Chiral solvating agent | | $^1$H NMR of a methyl | |
|---|---|---|---|---|
| | Type | NMR solvent (concentration mM) | group of rac-1-phenylethylamine (ppm) | Racemic separation |
| Example 9 ((b) in FIG. 1) | Metal complex H[Al-1b] prepared in Example 6 | CD$_3$OD (10) | 1.57, 1.52 | O |

TABLE 1-continued

| | Chiral solvating agent | | ¹H NMR of a methyl | |
| --- | --- | --- | --- | --- |
| | Type | NMR solvent (concentration mM) | group of rac-1-phenylethylamine (ppm) | Racemic separation |
| | *(structure: Al complex with Ph, O, N, H substituents)* | | | |
| Comparative Example 1 ((c) in FIG. 1) | D-Mandelic acid *(structure)* | CD₃OD (10) | 1.62 | X |
| Comparative Example 2 ((d) in FIG. 1) | Mecoprop-P *(structure)* | CD₃OD (10) | 1.62 | X |
| Comparative Example 3 ((e) in FIG. 1) | Dichloroprop-P *(structure)* | CD₃OD (10) | 1.62 | X |
| Comparative Example 4 ((f) in FIG. 1) | (−)-Pirkle's Alcohol *(structure)* | CD₃OD (10) | 1.38 | X |
| Comparative Example 5 ((g) in FIG. 1) | Eu(tfc)₃ *(structure)* | CD₃OD (10) | 1.38 | X |

TABLE 1-continued

| | Chiral solvating agent | | $^1$H NMR of a methyl | |
|---|---|---|---|---|
| | Type | NMR solvent (concentration mM) | group of rac-1-phenylethylamine (ppm) | Racemic separation |
| Comparative Example 6 ((h) in FIG. 1) | β-cyclodextrin | D$_2$O (10) | 1.41 | X |

It was confirmed that two enantiomers were separated only in the case of using the chiral solvating agent of the present invention (Example 9), as compared with the existing solvating agents (Comparative Examples 1 to 6).

Example 10 and Comparative Examples 7 to 14

Figure 2:
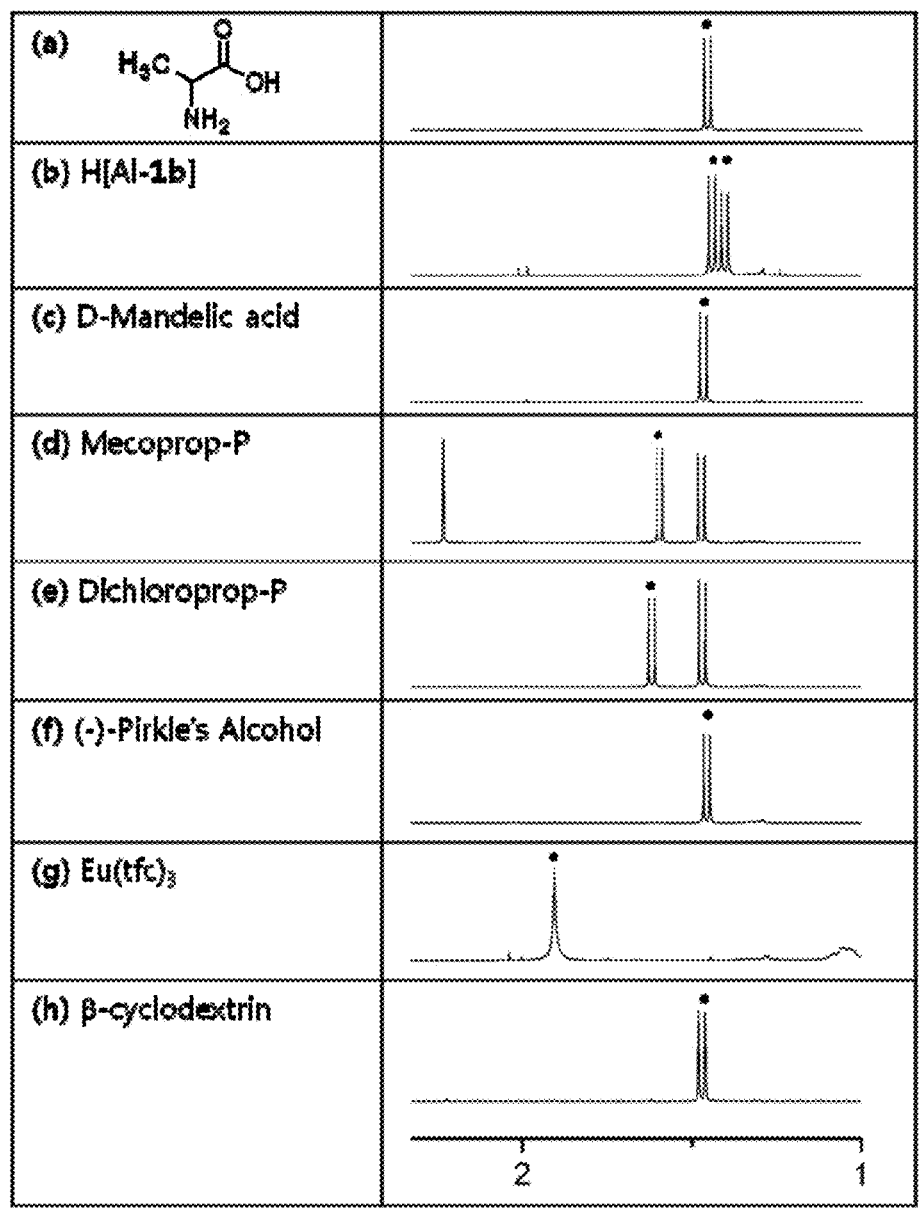
FIG. 2 is $^1$H NMR spectra of Example 10 and Comparative Examples 7 to 12.

Measurement of Optical Purity of DL-Alanine by $^1$H NMR Using Chiral Solvating Agents As shown in following Table 2, various chiral solvating agents and DL-alanine were dissolved in an NMR solvent at 25° C., and then measurement of $^1$H NMR spectra was carried out, thereby confirming whether two enantiomers are classified, and the results are illustrated in FIG. 2. (a) in FIG. 2 is $^1$H NMR of a methyl group of DL-alanine in CD$_3$OD.

TABLE 2

| | Chiral solvating agent | | $^1$H NMR of methyl group of DL-alanine (ppm) | Racemic separation |
|---|---|---|---|---|
| | Type | NMR solvent (concentration mM) | | |
| Example 10 ((b) in FIG. 2) | Metal complex H[Al-1b] prepared in Example 6 | CD$_3$OD (10) | 1.44, 1.40 | ○ |
| Comparative Example 7 ((c) in FIG. 2) | D-Mandelic acid | CD$_3$OD (10) | 1.47 | X |
| Comparative Example 8 ((d) in FIG. 2) | Mecoprop-P | CD$_3$OD (10) | 1.47 | X |
| Comparative Example 9 ((e) in FIG. 2) | Dichloroprop-P | CD$_3$OD (10) | 1.47 | X |
| Comparative Example 10 ((f) in FIG. 2) | (−)-Pirkle's Alcohol | CD$_3$OD (10) | 1.46 | X |
| Comparative Example 11 ((g) in FIG. 2) | Eu(tfc)$_3$ | CD$_3$OD (10) | 1.90 | X |
| Comparative Example 12 ((h) in FIG. 2) | β-cyclodextrin | D$_2$O (10) | 1.47 | X |

It was confirmed that two enantiomers were separated only in the case of using the chiral solvating agent of the present invention (Example 10), as compared with the existing solvating agents (Comparative Examples 7 to 12).

Example 11 and Comparative Examples 13 to 18

Figure 3:
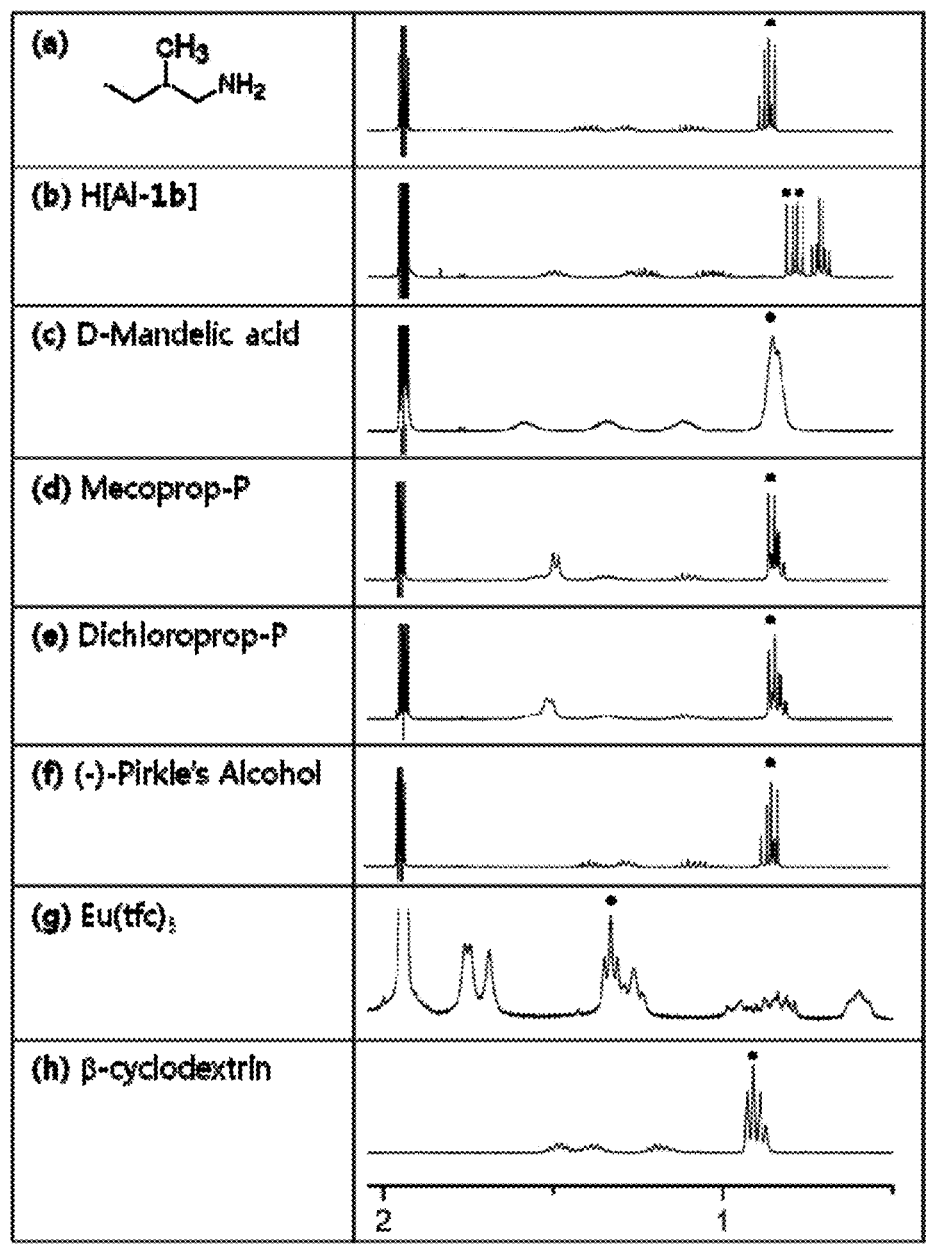
FIG. 3 is $^1$H NMR spectra of Example 11 and Comparative Examples 13 to 18.

Measurement of Optical Purity of Rac-2-Methylbutylamine by $^1$H NMR Using Chiral Solvating Agents As shown in following Table 3, various chiral solvating agents and rac-2-methylbutylamine were dissolved in an NMR solvent at 25° C., and then measurement of $^1$H NMR spectra was carried out, thereby confirming whether two enantiomers are classified, and the results are shown in the FIG. 3. (a) in FIG. 3 is $^1$H NMR of a methyl group of rac-2-methylbutylamine in.

TABLE 3

| | Chiral solvating agent | | $^1$H NMR of a methyl group of rac-2-methylbutylamine (ppm) | Racemic separation |
|---|---|---|---|---|
| | Type | NMR solvent (concentration mM) | | |
| Example 11 ((b) in FIG. 3) | Metal complex H[Al-1b] prepared in Example 6 | CD$_3$CN (10) | 0.80, 0.78 | ○ |
| Comparative Example 13 ((c) in FIG. 3) | D-Mandelic acid | CD$_3$CN (10) | 0.86 | X |
| Comparative Example 14 ((d) in FIG. 3) | Mecoprop-P | CD$_3$CN (10) | 0.85 | X |
| Comparative Example 15 ((e) in FIG. 3) | Dichloroprop-P | CD$_3$CN (10) | 0.86 | X |
| Comparative Example 16 ((f) in FIG. 3) | (−)-Pirkle's Alcohol | CD$_3$CN (10) | 0.84 | X |
| Comparative Example 17 ((g) in FIG. 3) | Eu(tfc)$_3$ | CD$_3$CN (10) | 1.33 | X |

TABLE 3-continued

| | Chiral solvating agent | | | |
|---|---|---|---|---|
| | Type | NMR solvent (concentration mM) | ¹H NMR of a methyl group of rac-2-methylbutylamine (ppm) | Racemic separation |
| Comparative Example 18 ((h) in FIG. 3) | β-cyclodextrin | D₂O (10) | 0.92 | X |

It was confirmed that two enantiomers were separated only in the case of using the chiral solvating agent of the present invention (Example 11), as compared with the existing solvating agents (Comparative Examples 13 to 18).

When the metal complex of the present invention H[Al-1b] is used as the chiral solvating agent, peak separation was observed in a polar protic solvent such as $CD_3OD$ or $CD_3CN$, differently from the case of using the chiral solvating agents conventionally known in the art, from the Examples and Comparative Examples.

Example 12

Measurement of Optical Purities of

Figure 4:
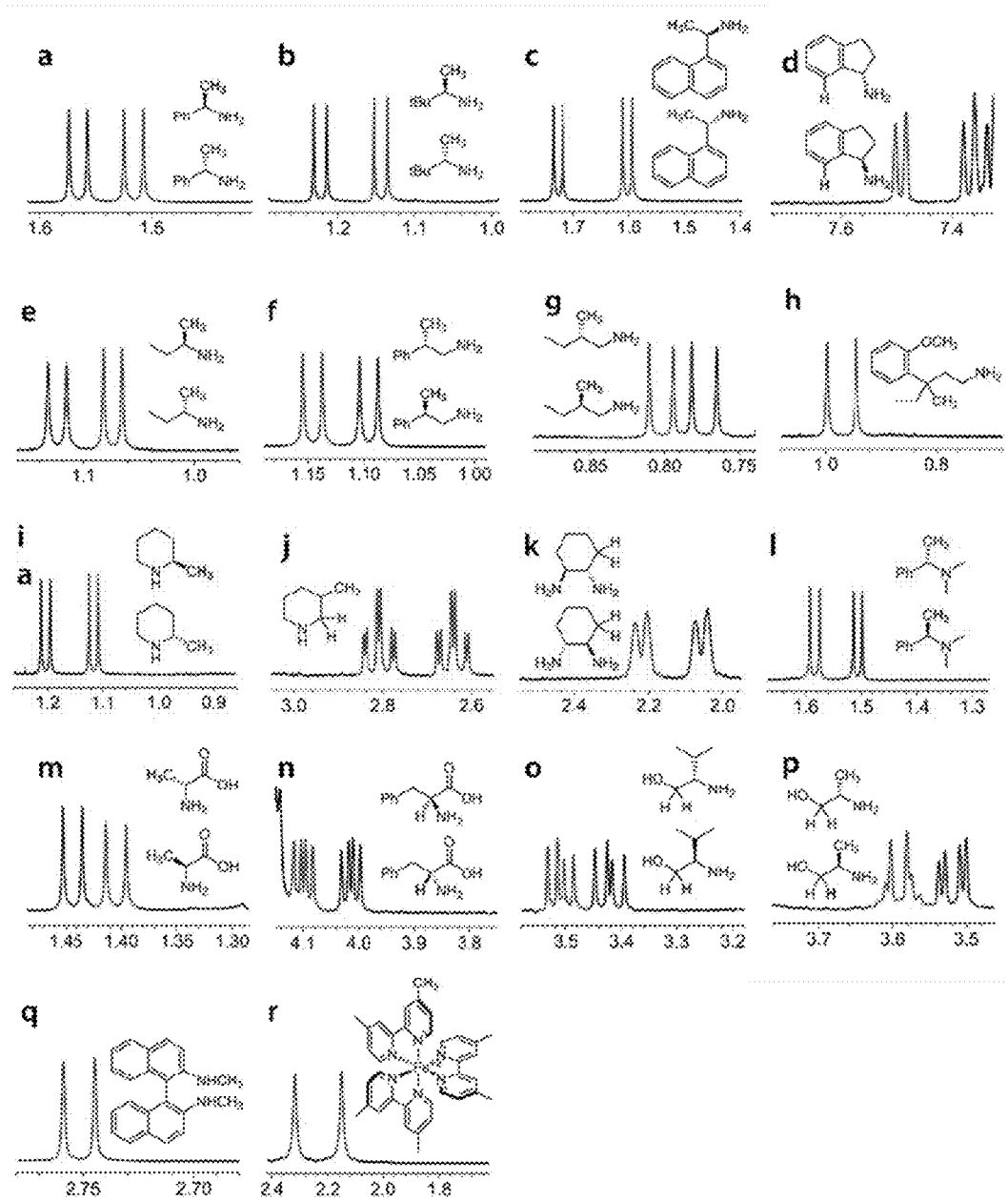
FIG. 4 is $^1$H NMR spectra of Example 12.

Amine or Positively Charged Compounds by ¹H NMR Using the Metal Complex H[Al-1b] of the Present Invention as a Chiral Solvating Agent In order to confirm the chiral solvation degree of the metal complex of the present invention, a 1:1 mixture of the metal complex H[Al-1b] of the present invention and a chiral analyte was dissolved in an NMR solvent to 20 mM at 25° C., and then measurement of ¹H NMR spectrum was carried out. The results are illustrated in FIG. 4.

As the chiral analyte, an amine compound or positively charged compounds were used, and as the amine compound, rac-1-phenylethylamine (a), rac-3,3-dimethylbutan-2-amine (b), rac-1-(1-naphthyl)ethylamine (c), rac-2,3-dihydro-1H-inden-1-amine (d), rac-2-methylbutylamine (e), rac-2-phenyl-1-propanamine (f), rac-2-methylbutan-1-amine (g), 3-(2-methoxyphenyl)-3-methylpentan-1-amine (h), rac-2-methylpiperidine (i), 3-methylpiperidine (j), rac-cyclohexane-1,2-diamine (k), rac-N,N-dimethyl-1-phenylethylamine (l), DL-alanine (m), DL-phenylalanine (n), DL-valinol (o), DL-alaninol (p), and N-methyl-1-(2-(methylamino)naphthalen-1-yl)naphthalen-2-amine (q) were used, as the positively charged compound, $[Fe(dmbp)_3]^{+2}$ (dmbp=4,4'-dimethyl-2,2'-bipyridine) was used, and as the NMR solvent, $CD_3OD$(a-d, i-n), $CD_3CN$(e-h, o-q) or $CDCl_3$ (r) was used.

Example 13

Figure 5:
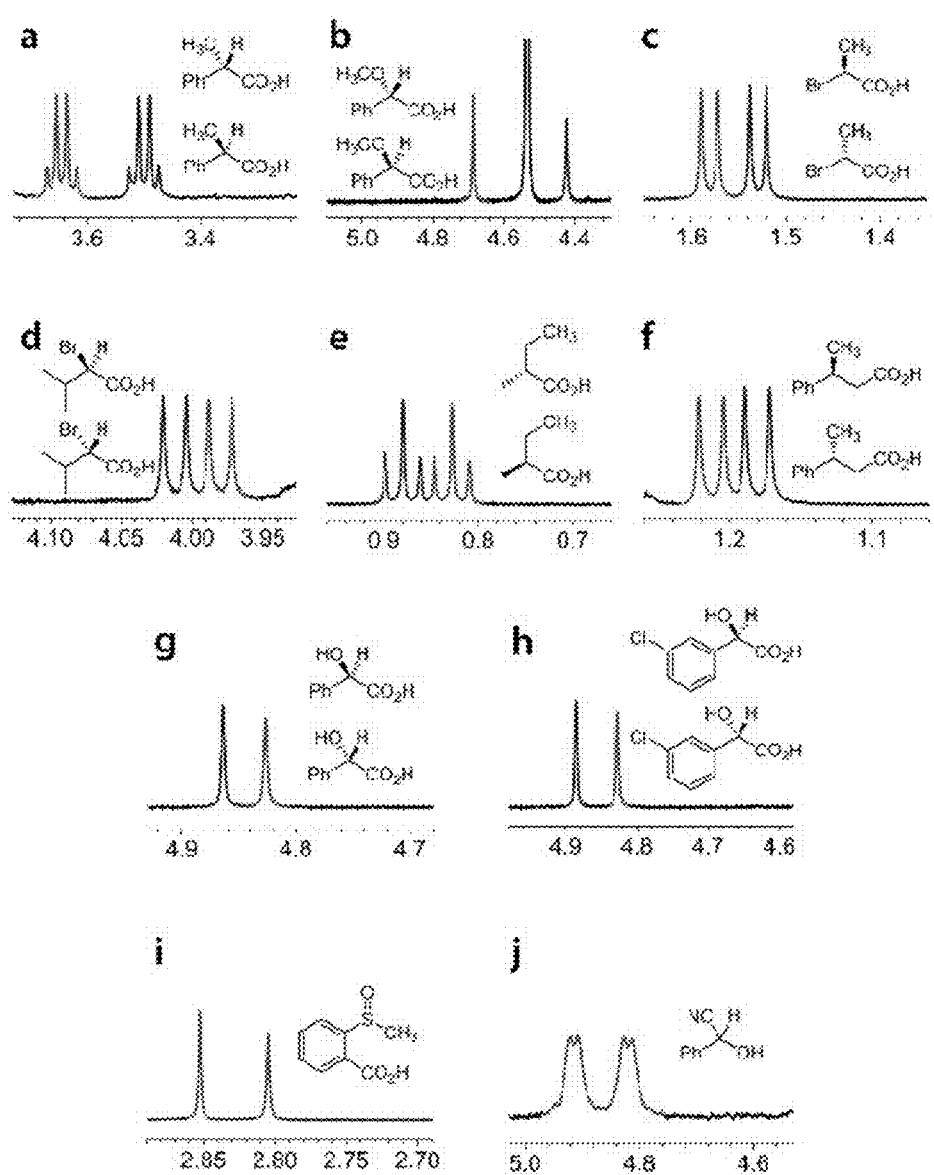
FIG. 5 is $^1$H NMR spectra of Example 13.

Measurement of Optical Purities of Carboxylic Acid Compounds by ¹H NMR Using the Metal Complex Na[Al-1b] of the Present Invention as a Chiral Solvating Agent In order to confirm the chiral solvation degree of the metal complex of the present invention, a 1:1 mixture of the metal complex Na[Al-1b] of the present invention and a carboxylic acid compound as a chiral analyte was dissolved in an NMR solvent to 20 mM at 25° C., and then measurement of ¹H NMR spectrum was carried out. The results are illustrated in FIG. 5.

As the carboxylic acid compound, rac-2-Phenylpropionic acid (a), rac-2-methoxy-2-phenylacetic acid (b), rac-2-bromopropionic acid (c), rac-2-bromo-3-methylbutanoic acid (d), rac-2-methylbutanoic acid (e), rac-3-phenylbutanoic acid (f), rac-mandelic acid (g), rac-3-chlorophenyl-2-hydroxyacetic acid (h), rac-2-(methylsulfinyl)benzoic acid (i), and rac-2-hydroxy-2-phenylacetonitrile (j) were used, and as the NMR solvent, $CDCl_3$ (a-f), $CD_3CN$ (g, h, j) or $CD_3OD$ (i) was used.

Example 14

Figure 6:
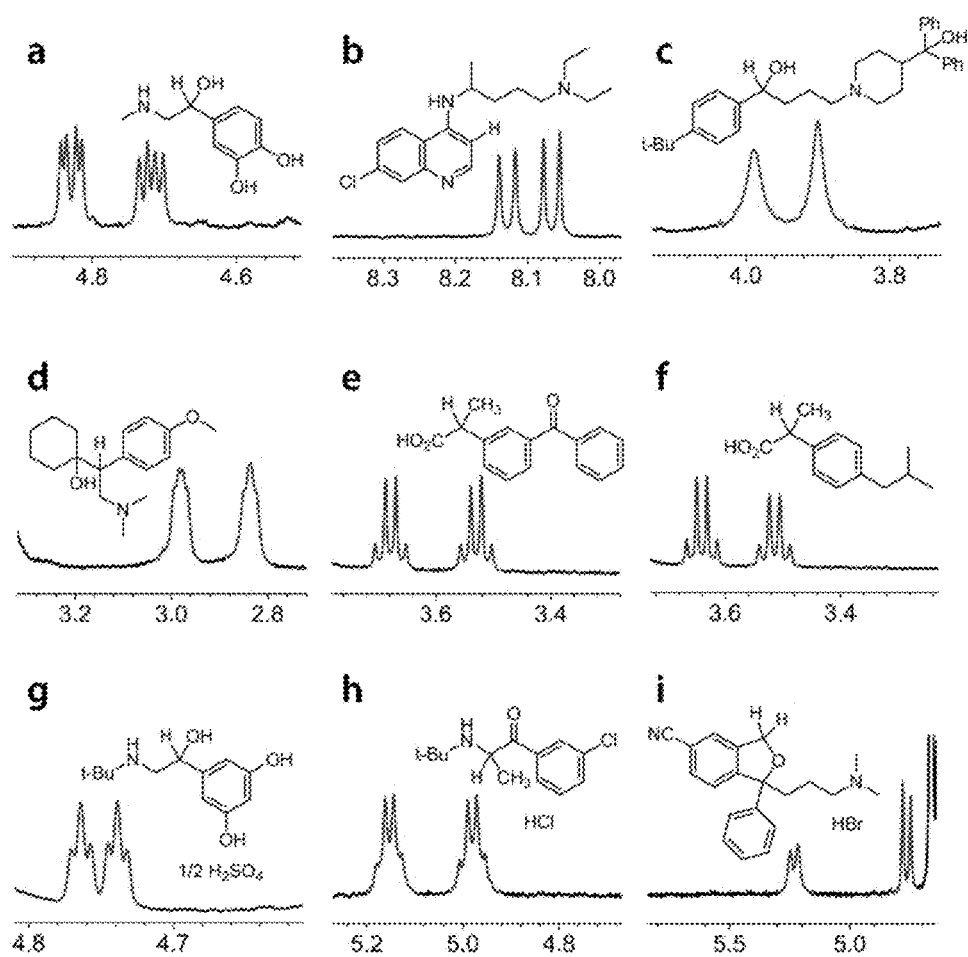
FIG. 6 is $^1$H NMR spectra of Example 14.

Measurement of Optical Purities of Commercial Drugs by ¹H NMR Using the Metal Complex M[Al-1b] (M=H⁺ or Na) of the Present Invention as a Chiral Solvating Agent In order to confirm the chiral solvation degree of the metal complex of the present invention, a 1:1 mixture of the metal complex M[Al-1b] (M=H⁺ or Na) of the present invention and a commercial drug as a chiral analyte was dissolved in an NMR solvent to 20 mM at 25° C., and then measurement of ¹H NMR spectrum was carried out. The results are illustrated in FIG. 6.

The commercial drugs are difficult to be subjected to chromatography analysis due to high polarity and low solubility in an organic solvent, and the commercial racemic drugs were used as the chiral analyte, and their structures are as follows:

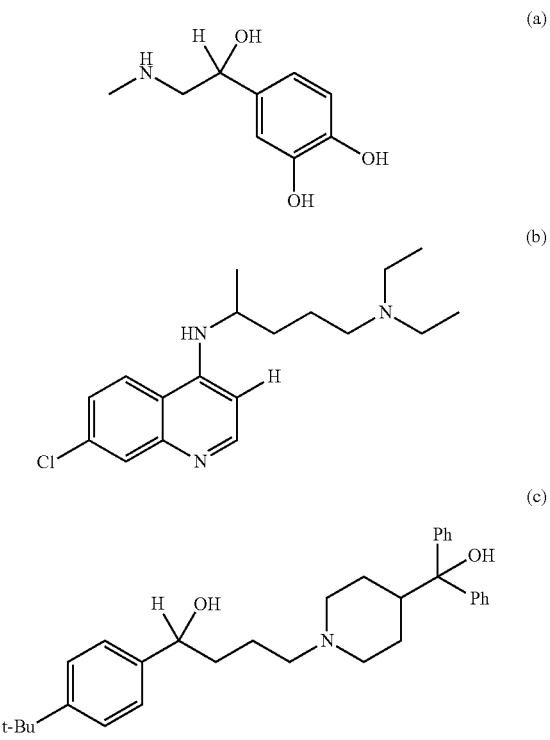

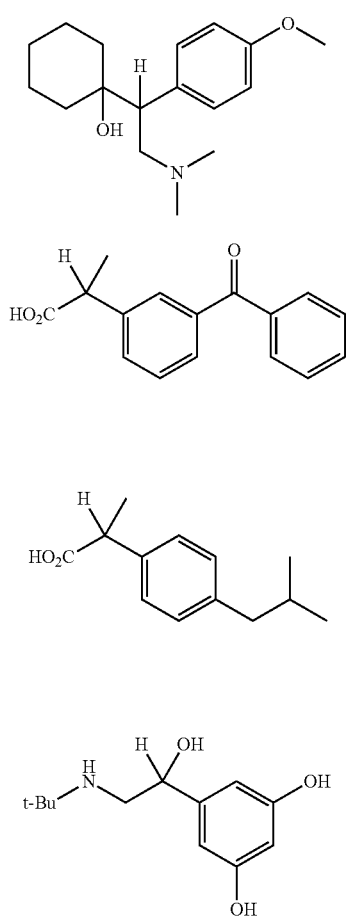

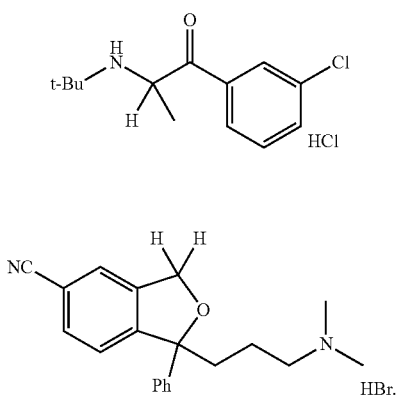

For the commercial drugs a-d, H[Al-1b] was used as the chiral solvating agent, and for the commercial drugs e-I, Na[Al-1b] was used as the chiral solvating agent. In addition, as the NMR solvent, $CD_3CN$ (a-c, h), $CDCl_3$ (e, f), $C_6D_6$ (d, i) or $CD_3OD$ (g) was used.

It is seen from the above Examples that the chirality of various chiral compounds such as various amine derivatives, carboxylic acid derivatives, cyanohydrin derivatives, charged metal complexes, and commercial racemic drugs may be analyzed by $^1$H NMR, in the case of using the metal complex of the present invention as the chiral solvating agent.

The chiral metal complex of the present invention is a chiral octahedral complex having a Δ or Λ configuration at a metal center due to the binding of the ligand of the Chemical formula 1, and it is possible to stereoselectively control Δ or Λ chirality at the metal center.

Further, the chiral metal complex of the present invention may be used as a highly efficient and practical chiral solvating agent in the measurement of the optical purity of all compounds charged with chiral charge which was regarded as being difficult to be subjected to chromatography analysis, such as a commercial racemic drug which is difficult to be subjected to chromatography analysis due to high polarity and low solubility in an organic solvent. Traditionally only the non-polar solvent was used so that the range of the analyte was extremely limited, however, in the present invention, the chiral metal complex is used as the chiral solvating agent, thereby allowing the polar solvent as well as the non-polar solvent to be used, and thus, even the analyte which has high polarity and was not able to be previously used as the analyte may be used.

Further, the chiral metal complex of the present invention may show sufficient peak separation to measure an optical purity in a polar solvent for measuring $^1$H NMR with only a sub-stoichiometric amount, and extend the stereocenter of the analyte from a charged functional group to δ position.

Accordingly, the chiral metal complex of the present invention may be used as a widely used chiral solvating agent for charged chiral compounds.

What is claimed is:

1. A $N_2O_2$ ligand having the following Chemical Formula 1:

[Chemical Formula 1]

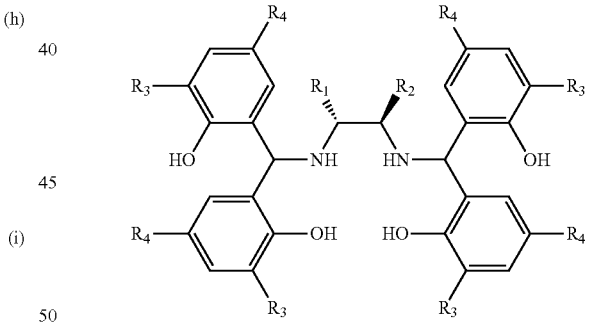

wherein $R_1$ and $R_2$ are independently of each other (C1-C10) alkyl or (C6-C20) aryl, or $R_1$ and $R_2$ are linked via (C2-C6) alkylene to form a cycloaliphatic ring; and $R_3$ and $R_4$ are independently of each other hydrogen, (C1-C10) alkyl, or halogen.

2. The $N_2O_2$ ligand of claim 1, wherein $R_1$ and $R_2$ are independently of each other methyl, ethyl, propyl, butyl, pentyl, hexyl, phenyl, biphenyl, naphthyl or anthryl, or $R_1$ and $R_2$ are linked via (C3-C4) alkylene to form a cycloaliphatic ring; and $R_3$ and $R_4$ are independently of each other hydrogen, methyl, ethyl, propyl, butyl, pentyl, hexyl, chloro, bromo or fluoro.

3. A metal complex having the following Chemical Formula 2:

[Chemical Formula 2]

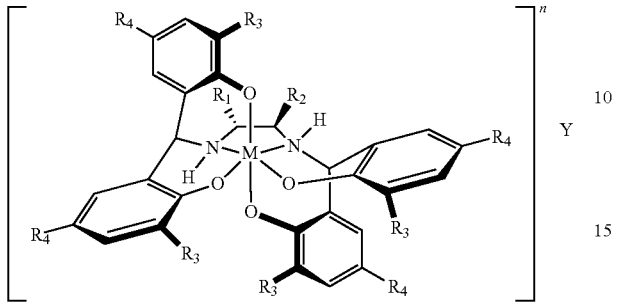

wherein
R₁ and R₂ are independently of each other (C1-C10) alkyl or (C6-C20) aryl, or R₁ and R₂ are linked via (C2-C6) alkylene to form a cycloaliphatic ring;
R₃ and R₄ are independently of each other hydrogen, (C1-C10) alkyl, or halogen;
when M is $Al^{3+}$ or $Sc^{3+}$, n is −1, and Y is $H^+$, $Li^+$, $Na^+$, $K^+$, $Ag^+$, $Cs^+$, $NR_4^+$, ½ $Mg^{2+}$, ½ $Ca^{2+}$, ½ $Zn^{2+}$ or ⅓ $Al^{3+}$; and
when M is $Ti^{4+}$, n is 0, and Y does not exist.

4. The metal complex of claim 3, wherein
R₁ and R₂ are independently of each other methyl, ethyl, propyl, butyl, pentyl, hexyl, phenyl, biphenyl, naphthyl or anthryl, or R₁ and R₂ are linked via (C3-C4) alkylene to form a cycloaliphatic ring;
R₃ and R₄ are independently of each other hydrogen, methyl, ethyl, propyl, butyl, pentyl, hexyl, chloro, bromo or fluoro;
when M is Al3+ or Sc3+, n is −1, and Y is H+ or Na+; and
when M is Ti4+, n is 0, and Y does not exist.

5. The metal complex of claim 3, wherein it is selected from following structures:

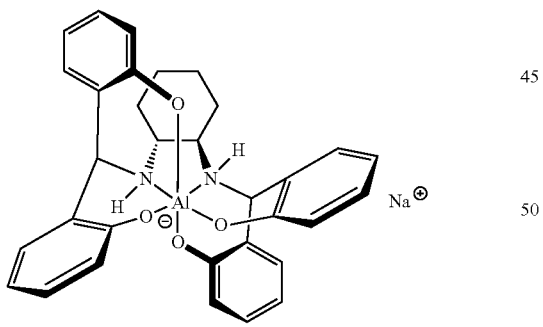

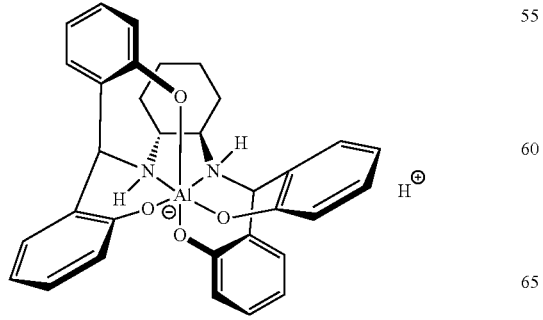

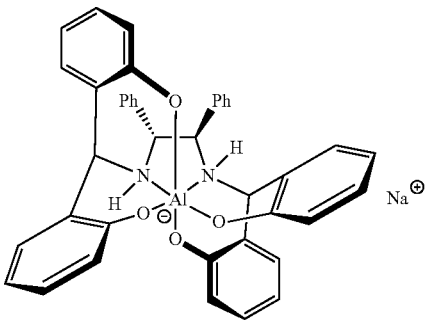

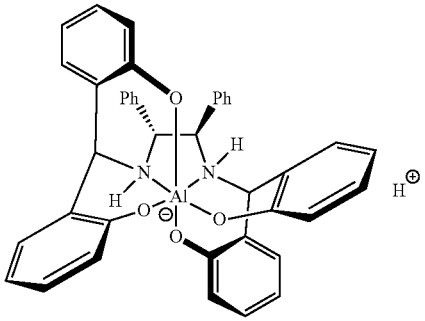

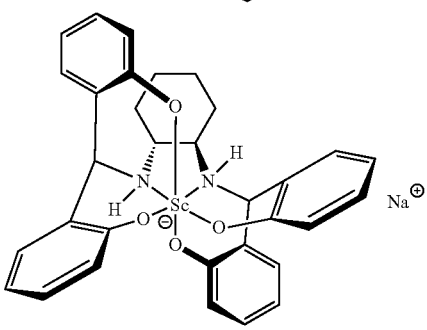

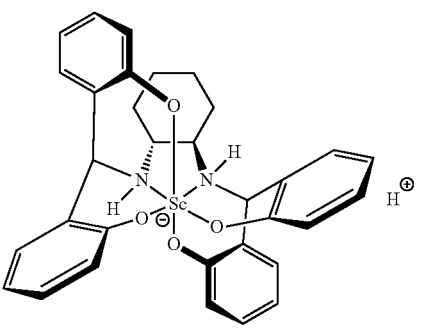

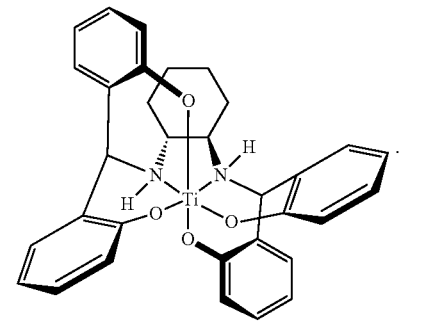

6. A method of measuring an optical purity of a chiral analyte, comprising the steps of combining the chiral metal complex of claim 3 as a chiral solvating agent with the chiral analyte and measuring the optical purity of the chiral analyte by nuclear magnetic resonance spectroscopy.

7. The method of claim 6, wherein the chiral metal complex is used in 0.5 to 10 equivalents relative to the chiral analyte.

\* \* \* \* \*